(12) United States Patent
Hayter et al.

(10) Patent No.: US 8,473,022 B2
(45) Date of Patent: Jun. 25, 2013

(54) ANALYTE SENSOR WITH TIME LAG COMPENSATION

(75) Inventors: Gary Hayter, Oakland, CA (US); Kenneth J. Doniger, Menlo Park, CA (US); Erwin S. Budiman, Fremont, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 949 days.

(21) Appl. No.: 12/363,706

(22) Filed: Jan. 30, 2009

(65) Prior Publication Data

US 2009/0198118 A1   Aug. 6, 2009

Related U.S. Application Data

(60) Provisional application No. 61/025,290, filed on Jan. 31, 2008.

(51) Int. Cl.
   *A61B 5/05*   (2006.01)

(52) U.S. Cl.
   USPC .......................... 600/347; 300/345; 300/365

(58) Field of Classification Search
   USPC ................................................. 600/347, 365
   See application file for complete search history.

(56) References Cited

U.S. PATENT DOCUMENTS

| | | |
|---|---|---|
| 3,581,062 A | 5/1971 | Aston |
| 3,926,760 A | 12/1975 | Allen et al. |
| 3,949,388 A | 4/1976 | Fuller |
| 4,036,749 A | 7/1977 | Anderson |
| 4,055,175 A | 10/1977 | Clemens et al. |
| 4,129,128 A | 12/1978 | McFarlane |
| 4,245,634 A | 1/1981 | Albisser et al. |
| 4,327,725 A | 5/1982 | Cortese et al. |
| 4,344,438 A | 8/1982 | Schultz |
| 4,349,728 A | 9/1982 | Phillips et al. |
| 4,373,527 A | 2/1983 | Fischell |
| 4,392,849 A | 7/1983 | Petre et al. |
| 4,425,920 A | 1/1984 | Bourland et al. |
| 4,431,004 A | 2/1984 | Bessman et al. |
| 4,478,976 A | 10/1984 | Goertz et al. |
| 4,494,950 A | 1/1985 | Fischell |
| 4,509,531 A | 4/1985 | Ward |
| 4,527,240 A | 7/1985 | Kvitash |
| 4,538,616 A | 9/1985 | Rogoff |
| 4,619,793 A | 10/1986 | Lee |
| 4,671,288 A | 6/1987 | Gough |

(Continued)

FOREIGN PATENT DOCUMENTS

| | | |
|---|---|---|
| DE | 4401400 | 7/1995 |
| EP | 0098592 | 1/1984 |

(Continued)

OTHER PUBLICATIONS

Armour, J. C., et al., "Application of Chronic Intravascular Blood Glucose Sensor in Dogs", *Diabetes*, vol. 39, 1990, pp. 1519-1526.

(Continued)

*Primary Examiner* — Patricia Mallari
*Assistant Examiner* — Michael D'Angelo
(74) *Attorney, Agent, or Firm* — Jackson & Co., LLP

(57) ABSTRACT

Methods and devices and systems for determining an analyte value are disclosed.

22 Claims, 8 Drawing Sheets

U.S. PATENT DOCUMENTS

| | | | |
|---|---|---|---|
| 4,703,756 A | 11/1987 | Gough et al. |
| 4,731,726 A | 3/1988 | Allen, III |
| 4,749,985 A | 6/1988 | Corsberg |
| 4,757,022 A | 7/1988 | Shults et al. |
| 4,777,953 A | 10/1988 | Ash et al. |
| 4,779,618 A | 10/1988 | Mund et al. |
| 4,854,322 A | 8/1989 | Ash et al. |
| 4,871,351 A | 10/1989 | Feingold |
| 4,890,620 A | 1/1990 | Gough |
| 4,925,268 A | 5/1990 | Iyer et al. |
| 4,953,552 A | 9/1990 | DeMarzo |
| 4,986,271 A | 1/1991 | Wilkins |
| 4,995,402 A | 2/1991 | Smith et al. |
| 5,000,180 A | 3/1991 | Kuypers et al. |
| 5,002,054 A | 3/1991 | Ash et al. |
| 5,019,974 A | 5/1991 | Beckers |
| 5,050,612 A | 9/1991 | Matsumura |
| 5,055,171 A | 10/1991 | Peck |
| 5,068,536 A | 11/1991 | Rosenthal |
| 5,082,550 A | 1/1992 | Rishpon et al. |
| 5,106,365 A | 4/1992 | Hernandez |
| 5,122,925 A | 6/1992 | Inpyn |
| 5,165,407 A | 11/1992 | Wilson et al. |
| 5,246,867 A | 9/1993 | Lakowicz et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,279,294 A | 1/1994 | Anderson et al. |
| 5,285,792 A | 2/1994 | Sjoquist et al. |
| 5,293,877 A | 3/1994 | O'Hara et al. |
| 5,299,571 A | 4/1994 | Mastrototaro |
| 5,320,725 A | 6/1994 | Gregg et al. |
| 5,322,063 A | 6/1994 | Allen et al. |
| 5,330,634 A | 7/1994 | Wong et al. |
| 5,340,722 A | 8/1994 | Wolfbeis et al. |
| 5,342,789 A | 8/1994 | Chick et al. |
| 5,356,786 A | 10/1994 | Heller et al. |
| 5,360,404 A | 11/1994 | Novacek et al. |
| 5,372,427 A | 12/1994 | Padovani et al. |
| 5,379,238 A | 1/1995 | Stark |
| 5,390,671 A | 2/1995 | Lord et al. |
| 5,391,250 A | 2/1995 | Cheney, II et al. |
| 5,408,999 A | 4/1995 | Singh et al. |
| 5,411,647 A | 5/1995 | Johnson et al. |
| 5,425,868 A | 6/1995 | Pedersen |
| 5,429,602 A | 7/1995 | Hauser |
| 5,431,160 A | 7/1995 | Wilkins |
| 5,431,921 A | 7/1995 | Thombre |
| 5,462,645 A | 10/1995 | Albery et al. |
| 5,497,772 A | 3/1996 | Schulman et al. |
| 5,505,828 A | 4/1996 | Wong et al. |
| 5,507,288 A | 4/1996 | Bocker et al. |
| 5,509,410 A | 4/1996 | Hill et al. |
| 5,514,718 A | 5/1996 | Lewis et al. |
| 5,531,878 A | 7/1996 | Vadgama et al. |
| 5,568,400 A | 10/1996 | Stark et al. |
| 5,568,806 A | 10/1996 | Cheney, II et al. |
| 5,569,186 A | 10/1996 | Lord et al. |
| 5,582,184 A | 12/1996 | Erickson et al. |
| 5,586,553 A | 12/1996 | Halili et al. |
| 5,593,852 A | 1/1997 | Heller et al. |
| 5,609,575 A | 3/1997 | Larson et al. |
| 5,628,310 A | 5/1997 | Rao et al. |
| 5,653,239 A | 8/1997 | Pompei et al. |
| 5,660,163 A | 8/1997 | Schulman et al. |
| 5,665,222 A | 9/1997 | Heller et al. |
| 5,711,001 A | 1/1998 | Bussan et al. |
| 5,711,861 A | 1/1998 | Ward et al. |
| 5,733,259 A | 3/1998 | Valcke et al. |
| 5,772,586 A | 6/1998 | Heinonen et al. |
| 5,791,344 A | 8/1998 | Schulman et al. |
| 5,842,189 A | 11/1998 | Keeler et al. |
| 5,899,855 A | 5/1999 | Brown |
| 5,925,021 A | 7/1999 | Castellano et al. |
| 5,935,224 A | 8/1999 | Svancarek et al. |
| 5,942,979 A | 8/1999 | Luppino |
| 5,957,854 A | 9/1999 | Besson et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,980,708 A | 11/1999 | Champagne et al. |
| 5,995,860 A | 11/1999 | Sun et al. |
| 6,001,067 A | 12/1999 | Shults et al. |
| 6,024,699 A | 2/2000 | Surwit et al. |
| 6,049,727 A | 4/2000 | Crothall |
| 6,083,710 A | 7/2000 | Heller et al. |
| 6,088,608 A | 7/2000 | Schulman et al. |
| 6,091,976 A | 7/2000 | Pfeiffer et al. |
| 6,093,172 A | 7/2000 | Funderburk et al. |
| 6,103,033 A | 8/2000 | Say et al. |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,134,461 A | 10/2000 | Say et al. |
| 6,162,611 A | 12/2000 | Heller et al. |
| 6,175,752 B1 | 1/2001 | Say et al. |
| 6,200,265 B1 | 3/2001 | Walsh et al. |
| 6,212,416 B1 | 4/2001 | Ward et al. |
| 6,219,574 B1 | 4/2001 | Cormier et al. |
| 6,233,471 B1 | 5/2001 | Berner et al. |
| 6,248,067 B1 | 6/2001 | Causey, III et al. |
| 6,275,717 B1 | 8/2001 | Gross et al. |
| 6,284,478 B1 | 9/2001 | Heller et al. |
| 6,293,925 B1 | 9/2001 | Safabash et al. |
| 6,295,506 B1 | 9/2001 | Heinonen et al. |
| 6,299,347 B1 | 10/2001 | Pompei |
| 6,306,104 B1 | 10/2001 | Cunningham et al. |
| 6,309,884 B1 | 10/2001 | Cooper et al. |
| 6,329,161 B1 | 12/2001 | Heller et al. |
| 6,360,888 B1 | 3/2002 | McIvor et al. |
| 6,366,794 B1 | 4/2002 | Moussy et al. |
| 6,377,828 B1 | 4/2002 | Chaiken et al. |
| 6,379,301 B1 | 4/2002 | Worthington et al. |
| 6,424,847 B1 | 7/2002 | Mastrototaro et al. |
| 6,427,088 B1 | 7/2002 | Bowman, IV et al. |
| 6,440,068 B1 | 8/2002 | Brown et al. |
| 6,478,736 B1 | 11/2002 | Mault |
| 6,484,046 B1 | 11/2002 | Say et al. |
| 6,514,718 B2 | 2/2003 | Heller et al. |
| 6,544,212 B2 | 4/2003 | Galley et al. |
| 6,551,494 B1 | 4/2003 | Heller et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,572,545 B2 | 6/2003 | Knobbe et al. |
| 6,576,101 B1 | 6/2003 | Heller et al. |
| 6,577,899 B2 | 6/2003 | Lebel et al. |
| 6,579,690 B1 | 6/2003 | Bonnecaze et al. |
| 6,585,644 B2 | 7/2003 | Lebel et al. |
| 6,591,125 B1 | 7/2003 | Buse et al. |
| 6,595,919 B2 | 7/2003 | Berner et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,633,772 B2 | 10/2003 | Ford et al. |
| 6,635,014 B2 | 10/2003 | Starkweather et al. |
| 6,648,821 B2 | 11/2003 | Lebel et al. |
| 6,654,625 B1 | 11/2003 | Say et al. |
| 6,656,114 B1 | 12/2003 | Poulsen et al. |
| 6,659,948 B2 | 12/2003 | Lebel et al. |
| 6,668,196 B1 | 12/2003 | Villegas et al. |
| 6,675,030 B2 | 1/2004 | Ciurczak et al. |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,698,269 B2 | 3/2004 | Baber et al. |

| Patent No. | Date | Inventor |
|---|---|---|
| 6,702,857 B2 | 3/2004 | Brauker et al. |
| 6,733,446 B2 | 5/2004 | Lebel et al. |
| 6,740,075 B2 | 5/2004 | Lebel et al. |
| 6,740,518 B1 | 5/2004 | Duong et al. |
| 6,741,877 B1 | 5/2004 | Shults et al. |
| 6,746,582 B2 | 6/2004 | Heller et al. |
| 6,758,810 B2 | 7/2004 | Lebel et al. |
| 6,770,030 B1 | 8/2004 | Schaupp et al. |
| 6,790,178 B1 | 9/2004 | Mault et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,862,465 B2 | 3/2005 | Shults et al. |
| 6,865,407 B2 | 3/2005 | Kimball et al. |
| 6,873,268 B2 | 3/2005 | Lebel et al. |
| 6,881,551 B2 | 4/2005 | Heller et al. |
| 6,882,940 B2 | 4/2005 | Potts et al. |
| 6,892,085 B2 | 5/2005 | McIvor et al. |
| 6,895,263 B2 | 5/2005 | Shin et al. |
| 6,895,265 B2 | 5/2005 | Silver |
| 6,931,327 B2 | 8/2005 | Goode, Jr. et al. |
| 6,932,894 B2 | 8/2005 | Mao et al. |
| 6,936,006 B2 | 8/2005 | Sabra |
| 6,950,708 B2 | 9/2005 | Bowman, IV et al. |
| 6,958,705 B2 | 10/2005 | Lebel et al. |
| 6,968,294 B2 | 11/2005 | Gutta et al. |
| 6,971,274 B2 | 12/2005 | Olin |
| 6,974,437 B2 | 12/2005 | Lebel et al. |
| 6,983,176 B2 | 1/2006 | Gardner et al. |
| 6,990,366 B2 | 1/2006 | Say et al. |
| 6,997,907 B2 | 2/2006 | Safabash et al. |
| 6,998,247 B2 | 2/2006 | Monfre et al. |
| 7,003,336 B2 | 2/2006 | Holker et al. |
| 7,003,340 B2 | 2/2006 | Say et al. |
| 7,003,341 B2 | 2/2006 | Say et al. |
| 7,022,072 B2 | 4/2006 | Fox et al. |
| 7,024,245 B2 | 4/2006 | Lebel et al. |
| 7,025,425 B2 | 4/2006 | Kovatchev et al. |
| 7,029,444 B2 | 4/2006 | Shin et al. |
| 7,041,068 B2 | 5/2006 | Freeman et al. |
| 7,052,483 B2 | 5/2006 | Wojcik |
| 7,056,302 B2 | 6/2006 | Douglas |
| 7,074,307 B2 | 7/2006 | Simpson et al. |
| 7,081,195 B2 | 7/2006 | Simpson et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,113,821 B1 | 9/2006 | Sun et al. |
| 7,118,667 B2 | 10/2006 | Lee |
| 7,134,999 B2 | 11/2006 | Brauker et al. |
| 7,136,689 B2 | 11/2006 | Shults et al. |
| 7,171,274 B2 | 1/2007 | Starkweather et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,225,535 B2 | 6/2007 | Feldman et al. |
| 7,226,978 B2 | 6/2007 | Tapsak et al. |
| 7,258,673 B2 | 8/2007 | Racchini et al. |
| 7,267,665 B2 | 9/2007 | Steil et al. |
| 7,276,029 B2 | 10/2007 | Goode, Jr. et al. |
| 7,278,983 B2 | 10/2007 | Ireland et al. |
| 7,299,082 B2 | 11/2007 | Feldman et al. |
| 7,310,544 B2 | 12/2007 | Brister et al. |
| 7,317,938 B2 | 1/2008 | Lorenz et al. |
| 7,335,294 B2 | 2/2008 | Heller et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,402,153 B2 | 7/2008 | Steil et al. |
| 7,404,796 B2 | 7/2008 | Ginsberg |
| 7,424,318 B2 | 9/2008 | Brister et al. |
| 7,460,898 B2 | 12/2008 | Brister et al. |
| 7,467,003 B2 | 12/2008 | Brister et al. |
| 7,471,972 B2 | 12/2008 | Rhodes et al. |
| 7,474,992 B2 | 1/2009 | Ariyur |
| 7,494,465 B2 | 2/2009 | Brister et al. |
| 7,497,827 B2 | 3/2009 | Brister et al. |
| 7,519,408 B2 | 4/2009 | Rasdal et al. |
| 7,547,281 B2 | 6/2009 | Hayes et al. |
| 7,569,030 B2 | 8/2009 | Lebel et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,613,491 B2 | 11/2009 | Boock et al. |
| 7,615,007 B2 | 11/2009 | Shults et al. |
| 7,618,369 B2 | 11/2009 | Hayter et al. |
| 7,632,228 B2 | 12/2009 | Brauker et al. |
| 7,637,868 B2 | 12/2009 | Saint et al. |
| 7,640,048 B2 | 12/2009 | Dobbles et al. |
| 7,651,596 B2 | 1/2010 | Petisce et al. |
| 7,653,425 B2 | 1/2010 | Hayter et al. |
| 7,654,956 B2 | 2/2010 | Brister et al. |
| 7,657,297 B2 | 2/2010 | Simpson et al. |
| 7,699,964 B2 | 4/2010 | Feldman et al. |
| 7,711,402 B2 | 5/2010 | Shults et al. |
| 7,713,574 B2 | 5/2010 | Brister et al. |
| 7,715,893 B2 | 5/2010 | Kamath et al. |
| 7,768,386 B2 | 8/2010 | Hayter et al. |
| 7,778,680 B2 | 8/2010 | Goode et al. |
| 7,920,906 B2 | 4/2011 | Goode et al. |
| 7,928,850 B2 | 4/2011 | Hayter et al. |
| 2002/0019022 A1 | 2/2002 | Dunn et al. |
| 2002/0042090 A1 | 4/2002 | Heller et al. |
| 2002/0068860 A1 | 6/2002 | Clark |
| 2002/0103499 A1 | 8/2002 | Perez et al. |
| 2002/0106709 A1 | 8/2002 | Potts et al. |
| 2002/0128594 A1 | 9/2002 | Das et al. |
| 2002/0161288 A1 | 10/2002 | Shin et al. |
| 2002/0169635 A1 | 11/2002 | Shillingburg |
| 2003/0004403 A1 | 1/2003 | Drinan et al. |
| 2003/0023317 A1 | 1/2003 | Brauker et al. |
| 2003/0032874 A1 | 2/2003 | Rhodes et al. |
| 2003/0042137 A1 | 3/2003 | Mao et al. |
| 2003/0065308 A1 | 4/2003 | Lebel et al. |
| 2003/0100821 A1 | 5/2003 | Heller et al. |
| 2003/0125612 A1 | 7/2003 | Fox et al. |
| 2003/0130616 A1 | 7/2003 | Steil et al. |
| 2003/0134347 A1 | 7/2003 | Heller et al. |
| 2003/0168338 A1 | 9/2003 | Gao et al. |
| 2003/0176933 A1 | 9/2003 | Lebel et al. |
| 2003/0187338 A1 | 10/2003 | Say et al. |
| 2003/0191377 A1 | 10/2003 | Robinson et al. |
| 2003/0199790 A1 | 10/2003 | Boecker et al. |
| 2003/0208113 A1 | 11/2003 | Mault et al. |
| 2003/0212317 A1 | 11/2003 | Kovatchev et al. |
| 2003/0212379 A1 | 11/2003 | Bylund et al. |
| 2003/0216630 A1 | 11/2003 | Jersey-Willuhn et al. |
| 2003/0217966 A1 | 11/2003 | Tapsak et al. |
| 2004/0010186 A1 | 1/2004 | Kimball et al. |
| 2004/0010207 A1 | 1/2004 | Flaherty et al. |
| 2004/0011671 A1 | 1/2004 | Shults et al. |
| 2004/0024553 A1 | 2/2004 | Monfre et al. |
| 2004/0039298 A1 | 2/2004 | Abreu |
| 2004/0040840 A1 | 3/2004 | Mao et al. |
| 2004/0045879 A1 | 3/2004 | Shults et al. |
| 2004/0064068 A1 | 4/2004 | DeNuzzio et al. |
| 2004/0106858 A1 | 6/2004 | Say et al. |
| 2004/0122353 A1 | 6/2004 | Shahmirian et al. |
| 2004/0133164 A1 | 7/2004 | Funderburk et al. |
| 2004/0138588 A1 | 7/2004 | Saikley et al. |
| 2004/0146909 A1 | 7/2004 | Duong et al. |
| 2004/0152622 A1 | 8/2004 | Keith et al. |
| 2004/0167464 A1 | 8/2004 | Ireland et al. |
| 2004/0167801 A1 | 8/2004 | Say et al. |
| 2004/0171921 A1 | 9/2004 | Say et al. |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193025 A1 | 9/2004 | Steil et al. |
| 2004/0193090 A1 | 9/2004 | Lebel et al. |
| 2004/0197846 A1 | 10/2004 | Hockersmith et al. |
| 2004/0199059 A1 | 10/2004 | Brauker et al. |
| 2004/0204687 A1 | 10/2004 | Mogensen et al. |
| 2004/0219664 A1 | 11/2004 | Heller et al. |
| 2004/0225338 A1 | 11/2004 | Lebel et al. |

| | | | | | | |
|---|---|---|---|---|---|---|
| 2004/0236200 A1 | 11/2004 | Say et al. | | 2006/0281985 A1 | 12/2006 | Ward et al. |
| 2004/0254433 A1 | 12/2004 | Bandis et al. | | 2007/0010950 A1 | 1/2007 | Abensour et al. |
| 2004/0267300 A1 | 12/2004 | Mace | | 2007/0016381 A1 | 1/2007 | Kamath et al. |
| 2005/0004439 A1 | 1/2005 | Shin et al. | | 2007/0027381 A1 | 2/2007 | Stafford |
| 2005/0004494 A1 | 1/2005 | Perez et al. | | 2007/0032706 A1 | 2/2007 | Kamath et al. |
| 2005/0010269 A1 | 1/2005 | Lebel et al. | | 2007/0033074 A1 | 2/2007 | Nitzan et al. |
| 2005/0027177 A1 | 2/2005 | Shin et al. | | 2007/0060803 A1 | 3/2007 | Liljeryd et al. |
| 2005/0027180 A1 | 2/2005 | Goode et al. | | 2007/0060814 A1 | 3/2007 | Stafford |
| 2005/0027181 A1 | 2/2005 | Goode et al. | | 2007/0066873 A1 | 3/2007 | Kamath et al. |
| 2005/0027462 A1 | 2/2005 | Goode et al. | | 2007/0071681 A1 | 3/2007 | Gadkar et al. |
| 2005/0027463 A1 | 2/2005 | Goode et al. | | 2007/0073129 A1 | 3/2007 | Shah et al. |
| 2005/0031689 A1 | 2/2005 | Shults et al. | | 2007/0078320 A1 | 4/2007 | Stafford |
| 2005/0038332 A1 | 2/2005 | Saidara et al. | | 2007/0078321 A1 | 4/2007 | Mazza et al. |
| 2005/0043598 A1 | 2/2005 | Goode, Jr. et al. | | 2007/0078322 A1 | 4/2007 | Stafford |
| 2005/0070777 A1 | 3/2005 | Cho et al. | | 2007/0078323 A1 | 4/2007 | Reggiardo et al. |
| 2005/0090607 A1 | 4/2005 | Tapsak et al. | | 2007/0094216 A1 | 4/2007 | Mathias et al. |
| 2005/0096511 A1 | 5/2005 | Fox et al. | | 2007/0100222 A1 | 5/2007 | Mastrototaro et al. |
| 2005/0096512 A1 | 5/2005 | Fox et al. | | 2007/0106135 A1 | 5/2007 | Sloan et al. |
| 2005/0112169 A1 | 5/2005 | Brauker et al. | | 2007/0118405 A1 | 5/2007 | Campbell et al. |
| 2005/0113653 A1 | 5/2005 | Fox et al. | | 2007/0124002 A1 | 5/2007 | Estes et al. |
| 2005/0114068 A1 | 5/2005 | Chey et al. | | 2007/0149875 A1 | 6/2007 | Ouyang et al. |
| 2005/0121322 A1 | 6/2005 | Say et al. | | 2007/0163880 A1 | 7/2007 | Woo et al. |
| 2005/0131346 A1 | 6/2005 | Douglas | | 2007/0168224 A1 | 7/2007 | Letzt et al. |
| 2005/0143635 A1 | 6/2005 | Kamath et al. | | 2007/0173706 A1 | 7/2007 | Neinast et al. |
| 2005/0176136 A1 | 8/2005 | Burd et al. | | 2007/0173761 A1 | 7/2007 | Kanderian et al. |
| 2005/0177398 A1 | 8/2005 | Watanabe et al. | | 2007/0179349 A1 | 8/2007 | Hoyme et al. |
| 2005/0182306 A1 | 8/2005 | Sloan | | 2007/0179352 A1 | 8/2007 | Randlov et al. |
| 2005/0187720 A1 | 8/2005 | Goode, Jr. et al. | | 2007/0191701 A1 | 8/2007 | Feldman et al. |
| 2005/0192494 A1 | 9/2005 | Ginsberg | | 2007/0203407 A1 | 8/2007 | Hoss et al. |
| 2005/0192557 A1 | 9/2005 | Brauker et al. | | 2007/0203966 A1 | 8/2007 | Brauker et al. |
| 2005/0195930 A1 | 9/2005 | Spital et al. | | 2007/0208246 A1* | 9/2007 | Brauker et al. ............... 600/365 |
| 2005/0199494 A1 | 9/2005 | Say et al. | | 2007/0213657 A1 | 9/2007 | Jennewine et al. |
| 2005/0203360 A1 | 9/2005 | Brauker et al. | | 2007/0235331 A1 | 10/2007 | Simpson et al. |
| 2005/0239154 A1 | 10/2005 | Feldman et al. | | 2007/0249922 A1 | 10/2007 | Peyser et al. |
| 2005/0241957 A1 | 11/2005 | Mao et al. | | 2007/0271285 A1 | 11/2007 | Eichorn et al. |
| 2005/0245795 A1 | 11/2005 | Goode, Jr. et al. | | 2007/0282299 A1 | 12/2007 | Hellwig |
| 2005/0245799 A1 | 11/2005 | Brauker et al. | | 2007/0299617 A1 | 12/2007 | Willis |
| 2005/0245839 A1 | 11/2005 | Stivoric et al. | | 2008/0009692 A1 | 1/2008 | Stafford |
| 2005/0245904 A1 | 11/2005 | Estes et al. | | 2008/0017522 A1 | 1/2008 | Heller et al. |
| 2005/0272985 A1 | 12/2005 | Kotulla et al. | | 2008/0021436 A1 | 1/2008 | Wolpert et al. |
| 2005/0287620 A1 | 12/2005 | Heller et al. | | 2008/0021666 A1 | 1/2008 | Goode, Jr. et al. |
| 2006/0001538 A1 | 1/2006 | Kraft et al. | | 2008/0029391 A1 | 2/2008 | Mao et al. |
| 2006/0004270 A1 | 1/2006 | Bedard et al. | | 2008/0033254 A1 | 2/2008 | Kamath et al. |
| 2006/0015020 A1 | 1/2006 | Neale et al. | | 2008/0039702 A1 | 2/2008 | Hayter et al. |
| 2006/0015024 A1 | 1/2006 | Brister et al. | | 2008/0045824 A1 | 2/2008 | Tapsak et al. |
| 2006/0016700 A1 | 1/2006 | Brister et al. | | 2008/0058625 A1 | 3/2008 | McGarraugh et al. |
| 2006/0019327 A1 | 1/2006 | Brister et al. | | 2008/0064937 A1 | 3/2008 | McGarraugh et al. |
| 2006/0020186 A1 | 1/2006 | Brister et al. | | 2008/0071156 A1 | 3/2008 | Brister et al. |
| 2006/0020187 A1 | 1/2006 | Brister et al. | | 2008/0071157 A1 | 3/2008 | McGarraugh et al. |
| 2006/0020188 A1 | 1/2006 | Kamath et al. | | 2008/0071158 A1 | 3/2008 | McGarraugh et al. |
| 2006/0020189 A1 | 1/2006 | Brister et al. | | 2008/0081977 A1 | 4/2008 | Hayter et al. |
| 2006/0020190 A1 | 1/2006 | Kamath et al. | | 2008/0083617 A1 | 4/2008 | Simpson et al. |
| 2006/0020191 A1 | 1/2006 | Brister et al. | | 2008/0086042 A1 | 4/2008 | Brister et al. |
| 2006/0020192 A1 | 1/2006 | Brister et al. | | 2008/0086044 A1 | 4/2008 | Brister et al. |
| 2006/0025663 A1 | 2/2006 | Talbot et al. | | 2008/0086273 A1 | 4/2008 | Shults et al. |
| 2006/0029177 A1 | 2/2006 | Cranford, Jr. et al. | | 2008/0097289 A1 | 4/2008 | Steil et al. |
| 2006/0031094 A1 | 2/2006 | Cohen et al. | | 2008/0108942 A1 | 5/2008 | Brister et al. |
| 2006/0036139 A1 | 2/2006 | Brister et al. | | 2008/0154513 A1 | 6/2008 | Kovatchev et al. |
| 2006/0036140 A1 | 2/2006 | Brister et al. | | 2008/0161666 A1 | 7/2008 | Feldman et al. |
| 2006/0036141 A1 | 2/2006 | Kamath et al. | | 2008/0167543 A1 | 7/2008 | Say et al. |
| 2006/0036142 A1 | 2/2006 | Brister et al. | | 2008/0172205 A1 | 7/2008 | Breton et al. |
| 2006/0036143 A1 | 2/2006 | Brister et al. | | 2008/0182537 A1 | 7/2008 | Manku et al. |
| 2006/0036144 A1 | 2/2006 | Brister et al. | | 2008/0183060 A1 | 7/2008 | Steil et al. |
| 2006/0036145 A1 | 2/2006 | Brister et al. | | 2008/0183061 A1 | 7/2008 | Goode et al. |
| 2006/0155180 A1 | 7/2006 | Brister et al. | | 2008/0183399 A1 | 7/2008 | Goode et al. |
| 2006/0156796 A1 | 7/2006 | Burke et al. | | 2008/0188731 A1 | 8/2008 | Brister et al. |
| 2006/0166629 A1 | 7/2006 | Reggiardo | | 2008/0188796 A1 | 8/2008 | Steil et al. |
| 2006/0173260 A1 | 8/2006 | Gaoni et al. | | 2008/0189051 A1 | 8/2008 | Goode et al. |
| 2006/0173406 A1 | 8/2006 | Hayes et al. | | 2008/0194935 A1 | 8/2008 | Brister et al. |
| 2006/0173444 A1 | 8/2006 | Choy et al. | | 2008/0194936 A1 | 8/2008 | Goode et al. |
| 2006/0183985 A1 | 8/2006 | Brister et al. | | 2008/0194937 A1 | 8/2008 | Goode et al. |
| 2006/0189863 A1 | 8/2006 | Peyser et al. | | 2008/0194938 A1 | 8/2008 | Brister et al. |
| 2006/0211072 A1 | 9/2006 | Ryan et al. | | 2008/0195232 A1 | 8/2008 | Carr-Brendel et al. |
| 2006/0222566 A1 | 10/2006 | Brauker et al. | | 2008/0195967 A1 | 8/2008 | Goode et al. |
| 2006/0224109 A1 | 10/2006 | Steil et al. | | 2008/0197024 A1 | 8/2008 | Simpson et al. |
| 2006/0229512 A1 | 10/2006 | Petisce et al. | | 2008/0200788 A1 | 8/2008 | Brister et al. |
| 2006/0247508 A1 | 11/2006 | Fennell | | 2008/0200789 A1 | 8/2008 | Brister et al. |
| 2006/0253296 A1 | 11/2006 | Liisberg et al. | | 2008/0200791 A1 | 8/2008 | Simpson et al. |
| 2006/0272652 A1 | 12/2006 | Stocker et al. | | 2008/0208025 A1 | 8/2008 | Shults et al. |

| | | |
|---|---|---|
| 2008/0208026 A1 | 8/2008 | Noujaim et al. |
| 2008/0208113 A1 | 8/2008 | Damiano et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0234663 A1 | 9/2008 | Yodfat et al. |
| 2008/0242961 A1 | 10/2008 | Brister et al. |
| 2008/0255434 A1 | 10/2008 | Hayter et al. |
| 2008/0255437 A1 | 10/2008 | Hayter |
| 2008/0255808 A1 | 10/2008 | Hayter |
| 2008/0256048 A1 | 10/2008 | Hayter |
| 2008/0262469 A1 | 10/2008 | Brister et al. |
| 2008/0275313 A1 | 11/2008 | Brister et al. |
| 2008/0287761 A1 | 11/2008 | Hayter |
| 2008/0287762 A1 | 11/2008 | Hayter |
| 2008/0287763 A1 | 11/2008 | Hayter |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0288180 A1 | 11/2008 | Hayter |
| 2008/0288204 A1 | 11/2008 | Hayter et al. |
| 2008/0296155 A1 | 12/2008 | Shults et al. |
| 2008/0306368 A1 | 12/2008 | Goode et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0312841 A1 | 12/2008 | Hayter |
| 2008/0312842 A1 | 12/2008 | Hayter |
| 2008/0312844 A1 | 12/2008 | Hayter et al. |
| 2008/0312845 A1 | 12/2008 | Hayter et al. |
| 2008/0314395 A1 | 12/2008 | Kovatchev et al. |
| 2008/0319279 A1 | 12/2008 | Ramsay et al. |
| 2009/0005665 A1 | 1/2009 | Hayter et al. |
| 2009/0006034 A1 | 1/2009 | Hayter et al. |
| 2009/0006133 A1 | 1/2009 | Weinert et al. |
| 2009/0012379 A1 | 1/2009 | Goode et al. |
| 2009/0018424 A1 | 1/2009 | Kamath et al. |
| 2009/0018425 A1 | 1/2009 | Ouyang et al. |
| 2009/0030294 A1 | 1/2009 | Petisce et al. |
| 2009/0033482 A1 | 2/2009 | Hayter et al. |
| 2009/0036747 A1 | 2/2009 | Hayter et al. |
| 2009/0036758 A1 | 2/2009 | Brauker et al. |
| 2009/0036760 A1 | 2/2009 | Hayter |
| 2009/0036763 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0055149 A1 | 2/2009 | Hayter et al. |
| 2009/0062633 A1 | 3/2009 | Brauker et al. |
| 2009/0062635 A1 | 3/2009 | Brauker et al. |
| 2009/0062767 A1 | 3/2009 | Van Antwerp et al. |
| 2009/0063402 A1 | 3/2009 | Hayter |
| 2009/0076356 A1 | 3/2009 | Simpson et al. |
| 2009/0076360 A1 | 3/2009 | Brister et al. |
| 2009/0076361 A1 | 3/2009 | Kamath et al. |
| 2009/0088614 A1 | 4/2009 | Taub et al. |
| 2009/0099436 A1 | 4/2009 | Brister et al. |
| 2009/0105560 A1 | 4/2009 | Solomon |
| 2009/0105636 A1 | 4/2009 | Hayter et al. |
| 2009/0124877 A1 | 5/2009 | Goode et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0164190 A1 | 6/2009 | Hayter |
| 2009/0164239 A1 | 6/2009 | Hayter et al. |
| 2009/0164251 A1 | 6/2009 | Hayter |
| 2009/0178459 A1 | 7/2009 | Li et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0198118 A1 | 8/2009 | Hayter et al. |
| 2009/0203981 A1 | 8/2009 | Brauker et al. |
| 2009/0204341 A1 | 8/2009 | Brauker et al. |
| 2009/0216103 A1 | 8/2009 | Brister et al. |
| 2009/0227855 A1 | 9/2009 | Hill et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0240440 A1 | 9/2009 | Shurabura et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0253973 A1 | 10/2009 | Bashan et al. |
| 2009/0287073 A1 | 11/2009 | Boock et al. |
| 2009/0287074 A1 | 11/2009 | Shults et al. |
| 2009/0292188 A1 | 11/2009 | Hoss et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0057040 A1 | 3/2010 | Hayter |
| 2010/0057041 A1 | 3/2010 | Hayter |
| 2010/0057042 A1 | 3/2010 | Hayter |
| 2010/0057044 A1 | 3/2010 | Hayter |
| 2010/0057057 A1 | 3/2010 | Hayter et al. |
| 2010/0063373 A1 | 3/2010 | Kamath et al. |
| 2010/0076283 A1 | 3/2010 | Simpson et al. |
| 2010/0081906 A1 | 4/2010 | Hayter et al. |
| 2010/0081908 A1 | 4/2010 | Dobbles et al. |
| 2010/0081910 A1 | 4/2010 | Brister et al. |
| 2010/0087724 A1 | 4/2010 | Brauker et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0119693 A1 | 5/2010 | Tapsak et al. |
| 2010/0121169 A1 | 5/2010 | Petisce et al. |
| 2010/0168546 A1 | 7/2010 | Kamath et al. |
| 2010/0191082 A1 | 7/2010 | Brister et al. |
| 2010/0240975 A1 | 9/2010 | Goode et al. |
| 2010/0312176 A1 | 12/2010 | Lauer et al. |

FOREIGN PATENT DOCUMENTS

| | | |
|---|---|---|
| EP | 0127958 | 12/1984 |
| EP | 0320109 | 6/1989 |
| EP | 0353328 | 2/1990 |
| EP | 0390390 | 10/1990 |
| EP | 0396788 | 11/1990 |
| EP | 0286118 | 1/1995 |
| EP | 1048264 | 11/2000 |

| | | |
|---|---|---|
| WO | WO-93/06237 | 4/1993 |
| WO | WO-96/25089 | 8/1996 |
| WO | WO-96/35370 | 11/1996 |
| WO | WO-98/35053 | 8/1998 |
| WO | WO-99/56613 | 11/1999 |
| WO | WO-00/49940 | 8/2000 |
| WO | WO-00/59370 | 10/2000 |
| WO | WO-00/78992 | 12/2000 |
| WO | WO-01/52935 | 7/2001 |
| WO | WO-01/54753 | 8/2001 |
| WO | WO-02/16905 | 2/2002 |
| WO | WO-02/058537 | 8/2002 |
| WO | WO-03/076893 | 9/2003 |
| WO | WO-03/082091 | 10/2003 |
| WO | WO-03/085372 | 10/2003 |
| WO | WO-2004/061420 | 7/2004 |
| WO | WO-2005/040404 | 5/2005 |
| WO | WO-2005/041766 | 5/2005 |
| WO | WO-2005/089103 | 9/2005 |
| WO | WO-2006/024671 | 3/2006 |
| WO | WO-2006/079114 | 7/2006 |
| WO | WO-2006/118947 | 11/2006 |
| WO | WO-2007/016399 | 2/2007 |
| WO | WO-2007/027788 | 3/2007 |
| WO | WO-2007/041069 | 4/2007 |
| WO | WO-2007/041070 | 4/2007 |
| WO | WO-2007/041248 | 4/2007 |
| WO | WO-2007/056638 | 5/2007 |
| WO | WO-2007/101223 | 9/2007 |
| WO | WO-2007/120363 | 10/2007 |
| WO | WO-2007/126444 | 11/2007 |
| WO | WO-2007/053832 | 12/2007 |
| WO | WO-2007/143225 | 12/2007 |
| WO | WO-2008/021913 | 2/2008 |
| WO | WO-2008/042760 | 4/2008 |
| WO | WO-2008/128210 | 10/2008 |
| WO | WO-2008/130896 | 10/2008 |
| WO | WO-2008/130897 | 10/2008 |
| WO | WO-2008/130898 | 10/2008 |
| WO | WO-2008/143943 | 11/2008 |
| WO | WO-2009/018058 | 2/2009 |
| WO | WO-2009/086216 | 7/2009 |
| WO | WO-2009/096992 | 8/2009 |
| WO | WO-2009/097594 | 8/2009 |

OTHER PUBLICATIONS

Bennion, N., et al., "Alternate Site Glucose Testing: A Crossover Design", *Diabetes Technology& Therapeutics*, vol. 4, No. 1, 2002, pp. 25-33.

Blank, T. B., et al., "Clinical Results From a Non-Invasive Blood Glucose Monitor", *Optical Diagnostics and Sensing of Biological Fluids and Glucose and Cholesterol Monitoring II, Proceedings of SPIE*, vol. 4624, 2002, pp. 1-10.

Brooks, S. L., et al., "Development of an On-Line Glucose Sensor for Fermentation Monitoring", *Biosensors*, vol. 3, 1987/88, pp. 45-56.

Cass, A. E., et al., "Ferrocene-Medicated Enzyme Electrode for Amperometric Determination of Glucose", *Analytical Chemistry*, vol. 56, No. 4, 1984, 667-671.

Csoregi, E., et al., "Design and Optimization of a Selective Subcutaneously Implantable Glucose Electrode Based on 'Wired' Glucose Oxidase", *Analytical Chemistry*, vol. 67, No. 7, 1995, pp. 1240-1244.

El-Khatib, F. H, et al., "Adaptive Closed-Loop Control Provides Blood-Glucose Regulation Using Subcutaneous Insulin and Glucagon Infusion in Diabetic Swine", *Journal of Diabetes Science and Technology*, vol. 1, No. 2, 2007, pp. 181-192.

Feldman, B., et al., "A Continuous Glucose Sensor Based Wired Enzyme™ Technology—Results from a 3-Day Trial in Patients with Type 1 Diabetes", *Diabetes Technology& Therapeutics*, vol. 5, No. 5, 2003, pp. 769-779.

Feldman, B., et al., "Correlation of Glucose Concentrations in Interstitial Fluid and Venous Blood During Periods of Rapid Glucose Change", *Abbott Diabetes Care, Inc. Freestyle Navigator Continuous Glucose Monitor Pamphlet*, 2004.

Isermann, R., "Supervision, Fault-Detection and Fault-Diagnosis Methods—An Introduction", *Control Engineering Practice*, vol. 5, No. 5, 1997, pp. 639-652.

Isermann, R., et al., "Trends in the Application of Model-Based Fault Detection and Diagnosis of Technical Processes", *Control Engineering Practice*, vol. 5, No. 5, 1997, pp. 709-719.

Johnson, P. C., "Peripheral Circulation", *John Wiley & Sons*, 1978, pp. 198.

Jungheim, K., et al., "How Rapid Does Glucose Concentration Change in Daily Life of Patients with Type 1 Diabetes?", 2002, pp. 250.

Jungheim, K., et al., "Risky Delay of Hypoglycemia Detection by Glucose Monitoring at the Arm", *Diabetes Care*, vol. 24, No. 7, 2001, pp. 1303-1304.

Kaplan, S. M., "Wiley Electrical and Electronics Engineering Dictionary", *IEEE Press*, 2004, pp. 141, 142, 548, 549.

Lortz, J., et al., "What is Bluetooth? We Explain the Newest Short-Range Connectivity Technology", *Smart Computing Learning Series, Wireless Computing*, vol. 8, Issue 5, 2002, pp. 72-74.

Malin, S. F., et al., "Noninvasive Prediction of Glucose by Near-Infrared Diffuse Reflectance Spectoscopy", *Clinical Chemistry*, vol. 45, No. 9, 1999, pp. 1651-1658.

McGarraugh, G., et al., "Glucose Measurements Using Blood Extracted from the Forearm and the Finger", *TheraSense, Inc.*, 2001, 16 Pages.

McGarraugh, G., et al., "Physiological Influences on Off-Finger Glucose Testing", *Diabetes Technology & Therapeutics*, vol. 3, No. 3, 2001, pp. 367-376.

McKean, B. D., et al., "A Telemetry-Instrumentation System for Chronically Implanted Glucose and Oxygen Sensors", *IEEE Transactions on Biomedical Engineering*, vol. 35, No. 7, 1988, pp. 526-532.

Pickup, J., et al., "Implantable Glucose Sensors: Choosing the Appropriate Sensing Strategy", *Biosensors*, vol. 3, 1987/88, pp. 335-346.

Pickup, J., et al., "In Vivo Molecular Sensing in Diabetes Mellitus: An Implantable Glucose Sensor with Direct Electron Transfer", *Diabetologia*, vol. 32, 1989, pp. 213-217.

Pishko, M. V., et al., "Amperometric Glucose Microelectrodes Prepared Through Immobilization of Glucose Oxidase in Redox Hydrogels", *Analytical Chemistry*, vol. 63, No. 20, 1991, pp. 2268-2272.

Quinn, C. P., et al., "Kinetics of Glucose Delivery to Subcutaneous Tissue in Rats Measured with 0.3-mm Amperometric Microsensors", *The American Physiological Society*, 1995, E155-E161.

Roe, J. N., et al., "Bloodless Glucose Measurements", *Critical Review in Therapeutic Drug Carrier Systems*, vol. 15, Issue 3, 1998, pp. 199-241.

Sakakida, M., et al., "Development of Ferrocene-Mediated Needle-Type Glucose Sensor as a Measure of True Subcutaneous Tissue Glucose Concentrations", *Artificial Organs Today*, vol. 2, No. 2, 1992, pp. 145-158.

Sakakida, M., et al., "Ferrocene-Mediated Needle-Type Glucose Sensor Covered with Newly Designed Biocompatible Membrane", *Sensors and Actuators B*, vol. 13-14, 1993, pp. 319-322.

Salehi, C., et al., "A Telemetry-Instrumentation System for Long-Term Implantable Glucose and Oxygen Sensors", *Analytical Letters*, vol. 29, No. 13, 1996, pp. 2289-2308.

Schmidtke, D. W., et al., "Measurement and Modeling of the Transient Difference Between Blood and Subcutaneous Glucose Concentrations in the Rat After Injection of Insulin", *Proceedings of the National Academy of Sciences*, vol. 95, 1998, pp. 294-299.

Shaw, G. W., et al., "In Vitro Testing of a Simply Constructed, Highly Stable Glucose Sensor Suitable for Implantation in Diabetic Patients", *Biosensors & Bioelectronics*, vol. 6, 1991, pp. 401-406.

Shichiri, M., et al., "Glycaemic Control in Pancreatectomized Dogs with a Wearable Artificial Endocrine Pancreas", *Diabetologia*, vol. 24, 1983, pp. 179-184.

Shichiri, M., et al., "In Vivo Characteristics of Needle-Type Glucose Sensor—Measurements of Subcutaneous Glucose Concentrations in Human Volunteers", *Hormone and Metabolic Research Supplement Series*, vol. 20, 1988, pp. 17-20.

Shichiri, M., et al., "Membrane Design for Extending the Long-Life of an Implantable Glucose Sensor", *Diabetes Nutrition and Metabolism*, vol. 2, 1989, pp. 309-313.

Shichiri, M., et al., "Needle-type Glucose Sensor for Wearable Artificial Endocrine Pancreas", *Implantable Sensors for Closed-Loop Prosthetic Systems*, Chapter 15, 1985, pp. 197-210.

Shichiri, M., et al., "Telemetry Glucose Monitoring Device With Needle-Type Glucose Sensor: A Useful Tool for Blood Glucose Monitoring in Diabetic Individuals", *Diabetes Care*, vol. 9, No. 3, 1986, pp. 298-301.

Shichiri, M., et al., "Wearable Artificial Endocrine Pancreas With Needle-Type Glucose Sensor", *The Lancet*, 1982, pp. 1129-1131.

Shults, M. C., et al., "A Telemetry-Instrumentation System for Monitoring Multiple Subcutaneously Implanted Glucose Sensors", *IEEE Transactions on Biomedical Engineering*, vol. 41, No. 10, 1994, pp. 937-942.

Sternberg, R., et al., "Study and Development of Multilayer Needle-Type Enzyme-Based Glucose Microsensors", *Biosensors*, vol. 4, 1988, pp. 27-40.

Thompson, M., et al., "In Vivo Probes: Problems and Perspectives", *Clinical Biochemistry*, vol. 19, 1986, pp. 255-261.

Turner, A., et al., "Diabetes Mellitus: Biosensors for Research and Management", *Biosensors*, vol. 1, 1985, pp. 85-115.

Updike, S. J., et al., "Principles of Long-Term Fully Implanted Sensors with Emphasis on Radiotelemetric Monitoring of Blood Glucose from Inside a Subcutaneous Foreign Body Capsule (FBC)", Biosensors in the Body: Continuous in vivo Monitoring, Chapter 4, 1997, pp. 117-137.

Velho, G., et al., "Strategies for Calibrating a Subcutaneous Glucose Sensor", *Biomedica Biochimica Acta*, vol. 48, 1989, pp. 957-964.

Wilson, G. S., et al., "Progress Toward the Development of an Implantable Sensor for Glucose", *Clinical Chemistry*, vol. 38, No. 9, 1992, pp. 1613-1617.

Aussedat, B., et al., "A User-Friendly Method for Calibrating a Subcutaneous Glucose Sensor-Based Hypoglycaemic Alarm", *Biosensors & Bioelectronics*, vol. 12, No. 11, 1997, pp. 1061-1070.

Garg, S., et al., "Improvement in Glycemic Excusions with a Transcutaneous, Real-Time Continuous Glucose Sensor", *Diabetes Care*, vol. 29, No. 1, 2006, pp. 44-50.

Mougiakakou, et al., "A Real Time Simulation Model of Glucose-Insulin Metabolism for Type 1 Diabetes Patients", *Proceedings of the 2005 IEEE*, 2005, pp. 298-301.

U.S. Appl. No. 12/257,356, Office Action mailed Nov. 25, 2011.

* cited by examiner

ANALYTE SENSOR WITH TIME LAG COMPENSATION

RELATED APPLICATIONS

The present application claims priority under §35 U.S.C. 119(e) to U.S. Provisional Application No. 61/025,290 filed Jan. 31, 2008, and is related to application Ser. No. 11/537,991 filed on Oct. 2, 2006, each assigned to the Assignee of the present application Abbott Diabetes Care, Inc., of Alameda, Calif., the disclosures of each of which are incorporated herein by reference for all purposes.

BACKGROUN

Analyte, e.g., glucose monitoring systems including continuous and discrete monitoring systems generally include a small, lightweight battery powered and microprocessor controlled system which is configured to detect signals proportional to the corresponding measured glucose levels using an electrometer, and RF signals to transmit the collected data. One aspect of certain analyte monitoring systems include a transcutaneous or subcutaneous analyte sensor configuration which is, for example, partially mounted on the skin of a subject whose analyte level is to be monitored. The sensor cell may use a two or three-electrode (work, reference and counter electrodes) configuration driven by a controlled potential (potentiostat) analog circuit connected through a contact system.

The analyte sensor may be configured so that at least a portion thereof is placed under the skin of the patient so as to detect the analyte levels of the patient. In embodiments in which a portion is below the skin and a portion is above, the portion above the skin may be directly or indirectly connected with the transmitter unit. The transmitter unit is configured to transmit the analyte levels, e.g., in the form of current, detected by the sensor over a wireless (or wired) communication link such as an RF (radio frequency) communication link to a receiver/monitor unit. The receiver/monitor unit performs data analysis, among others on the received analyte levels to generate information pertaining to the monitored analyte levels.

To obtain accurate data from the analyte sensor, calibration may be necessary. In certain instances, blood glucose measurements are periodically obtained using, for example, a conventional analyte test strip and blood glucose meter, and the measured blood glucose values are used to calibrate the sensors. Indeed, the patient may calibrate each new analyte sensor using for example, capillary blood glucose measurements. Due to a lag factor between the monitored data and the measured blood glucose values, an error may be introduced in the monitored data.

In view of the foregoing, it would be desirable to have a method and system for calibrating analyte sensors of an analyte monitoring system to account for such lag errors in analyte monitoring systems.

SUMMARY OF THE INVENTION

In one embodiment, methods including determining a calibration parameter associated with a detected analyte value, calibrating the analyte value based on the calibration parameter, and dynamically updating the calibration parameter is disclosed. Devices, systems and algorithms (e.g., embodied on computer readable medium) for performing such methods are also provided.

These and other objects, features and advantages of the present disclosure will become more fully apparent from the following detailed description of the embodiments, the appended claims and the accompanying drawings.

DETAILED DESCRIPTION

As described in further detail below, in accordance with the various embodiments of the present disclosure, there is provided a method and system for calibration of analyte sensors to reduce errors in the sensor measurements. In particular, within the scope of the present disclosure, there are provided method and system for calibrating subcutaneous or transcutaneously positioned analyte sensors to compensate for time lag errors associated with an analyte sensor.

Figure 1:
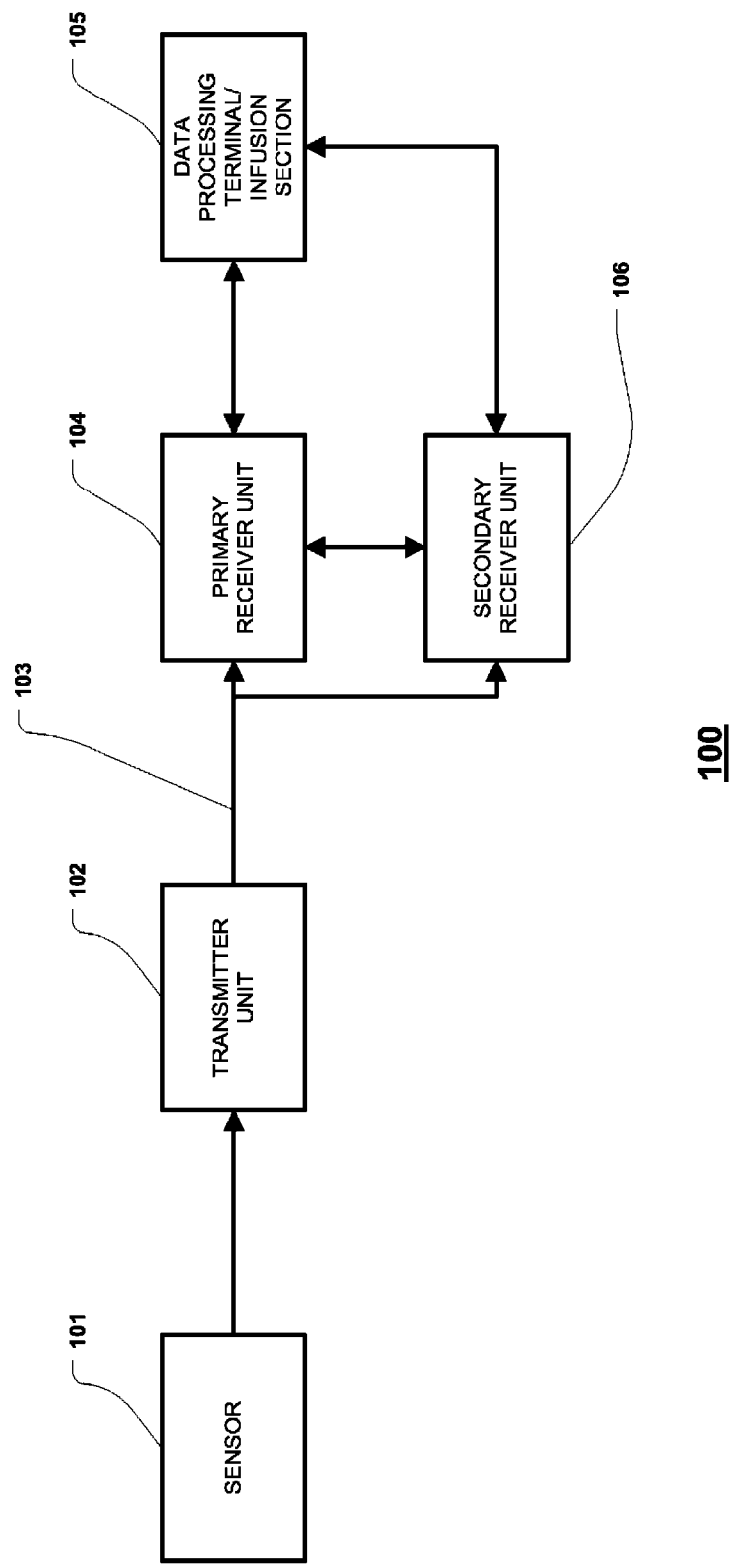
FIG. 1 illustrates a block diagram of a data monitoring and management system for practicing one or more embodiments of the present disclosure.

FIG. 1 illustrates a data monitoring and management system such as, for example, analyte (e.g., glucose) monitoring system 100 in accordance with one embodiment of the present disclosure. The subject invention is further described primarily with respect to a glucose monitoring system for convenience and such description is in no way intended to limit the scope of the invention. It is to be understood that the analyte monitoring system may be configured to monitor a variety of analytes, e.g., lactate, and the like. For example, analytes that may be monitored include but are not limited to, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored.

The analyte monitoring system 100 includes a sensor 101, a transmitter unit 102 directly or indirectly coupled to the sensor 101, and a primary receiver unit 104 which is configured to communicate with the transmitter unit 102 via a communication link 103. The primary receiver unit 104 may be further configured to transmit data to a data processing terminal 105 for evaluating the data received by the primary receiver unit 104. Moreover, the data processing terminal in one embodiment may be configured to receive data directly from the transmitter unit 102 via a communication link which may optionally be configured for bi-directional communication.

Also shown in FIG. 1 is an optional secondary receiver unit 106 which is operatively coupled to the communication link and configured to receive data transmitted from the transmitter unit 102. Moreover, as shown in the Figure, the secondary receiver unit 106 is configured to communicate with the primary receiver unit 104 as well as the data processing terminal 105. Indeed, the secondary receiver unit 106 may be configured for bi-directional wireless communication with each of the primary receiver unit 104 and the data processing terminal 105. As discussed in further detail below, in one embodiment of the present disclosure, the secondary receiver unit 106 may be configured to include a limited number of functions and features as compared with the primary receiver unit 104. As such, the secondary receiver unit 106 may be configured substantially in a smaller compact housing or embodied in a device such as a wrist watch, for example. Alternatively, the secondary receiver unit 106 may be configured with the same or substantially similar functionality as the primary receiver unit 104, and may be configured to be used in conjunction with a docking cradle unit for placement by bedside, for night time monitoring, and/or bi-directional communication device.

Only one sensor 101, transmitter unit 102, communication link 103, and data processing terminal 105 are shown in the embodiment of the analyte monitoring system 100 illustrated in FIG. 1. However, it will be appreciated by one of ordinary skill in the art that the analyte monitoring system 100 may include one or more sensor 101, transmitter unit 102, communication link 103, and data processing terminal 105. Moreover, within the scope of the present disclosure, the analyte monitoring system 100 may be a continuous monitoring system, or semi-continuous, or a discrete monitoring system. In a multi-component environment, each device is configured to be uniquely identified by each of the other devices in the system so that communication conflict is readily resolved between the various components within the analyte monitoring system 100.

In one embodiment of the present disclosure, the sensor 101 is physically positioned in or on the body of a user whose analyte level is being monitored. In one aspect, the sensor 101 may be configured to use one or more of coulometric, amperometric, potentiometric or conductimetric approaches to measure the analyte level being monitored. The sensor 101 may be configured to continuously sample the analyte of the user and the sampled analyte may be converted into a corresponding data signal for transmission by the transmitter unit 102. In one embodiment, the transmitter unit 102 is mounted on the sensor 101 so that both devices are positioned on the user's body. The transmitter unit 102 performs data processing such as filtering and encoding on data signals, each of which corresponds to a sampled analyte level of the user, for transmission to the primary receiver unit 104 via the communication link 103.

In one embodiment, the analyte monitoring system 100 is configured as a one-way RF communication path from the transmitter unit 102 to the primary receiver unit 104. In such embodiment, the transmitter unit 102 may transmit the sampled data signals received from the sensor 101 without acknowledgement from the primary receiver unit 104 that the transmitted sampled data signals have been received (in other embodiments there may be acknowledgement). For example, the transmitter unit 102 may be configured to transmit the encoded sampled data signals at a fixed rate (e.g., at one minute intervals or other interval) after the completion of the initial power on procedure. Likewise, the primary receiver unit 104 may be configured to detect such transmitted encoded sampled data signals at predetermined time intervals. Alternatively, the analyte monitoring system 100 may be configured with a bi-directional RF (or otherwise) communication between the transmitter unit 102 and the primary receiver unit 104.

Additionally, in one aspect, the primary receiver unit 104 may include two sections. The first section is an analog interface section that is configured to communicate with the transmitter unit 102 via the communication link 103. In one embodiment, the analog interface section may include an RF receiver and an antenna for receiving and amplifying the data signals from the transmitter unit 102, which are thereafter, demodulated with a local oscillator and filtered through a band-pass filter. The second section of the primary receiver unit 104 is a data processing section which is configured to process the data signals received from the transmitter unit 102 such as by performing data decoding, error detection and correction, data clock generation, and data bit recovery.

In operation in certain embodiments, upon completing a power-on procedure if required, the primary receiver unit 104 is configured to detect the presence of the transmitter unit 102 within its range based on, for example, the strength of the detected data signals received from the transmitter unit 102 or a predetermined transmitter identification information. Upon successful synchronization with the corresponding transmitter unit 102, the primary receiver unit 104 is configured to begin receiving from the transmitter unit 102 data signals corresponding to the user's detected analyte level. More specifically, the primary receiver unit 104 in one embodiment is configured to perform synchronized time hopping with the corresponding synchronized transmitter unit 102 via the communication link 103 to obtain the user's detected analyte level.

Referring again to FIG. 1, the data processing terminal 105 may include a personal computer, a portable computer such as a laptop or a handheld device (e.g., personal digital assistants (PDAs), telephone such as a cellular telephone), and the like, each of which may be configured for data communication with the receiver via a wired or a wireless connection. Additionally, the data processing terminal 105 may further be connected to a data network (not shown) for storing, retrieving and updating data corresponding to the detected analyte level of the user.

Within the scope of the present disclosure, the data processing terminal 105 may include an infusion device such as an insulin infusion pump or the like, which may be configured to administer a drug such as, for example insulin, to users, and which may be configured to communicate with the receiver unit 104 for receiving, among others, the measured analyte level. Alternatively, the receiver unit 104 may be configured to integrate an infusion device therein so that the receiver unit 104 is configured to administer insulin therapy to patients, for example, for administering and modifying basal profiles, as well as for determining appropriate boluses for administration based on, among others, the detected analyte levels received from the transmitter unit 102.

Additionally, the transmitter unit 102, the primary receiver unit 104 and the data processing terminal 105 may each be configured for bi-directional wireless communication such that each of the transmitter unit 102, the primary receiver unit 104 and the data processing terminal 105 may be configured to communicate (that is, transmit data to and receive data from) with each other via the wireless communication link 103. More specifically, the data processing terminal 105 may in one embodiment be configured to receive data directly from the transmitter unit 102 via a communication link, where the communication link, as described above, may be configured for bi-directional communication.

In this embodiment, the data processing terminal 105 which may include an insulin pump, may be configured to receive the analyte signals from the transmitter unit 102, and thus, incorporate the functions of the receiver 104 including data processing for managing the patient's insulin therapy and analyte monitoring. In one embodiment, the communication link 103 may include one or more of an RF communication protocol, an infrared communication protocol, a Bluetooth® enabled communication protocol, an 802.11x wireless communication protocol, or an equivalent wireless communication protocol which would allow secure, wireless communication of several units (for example, per HIPAA requirements) while avoiding potential data collision and interference.

Figure 2:
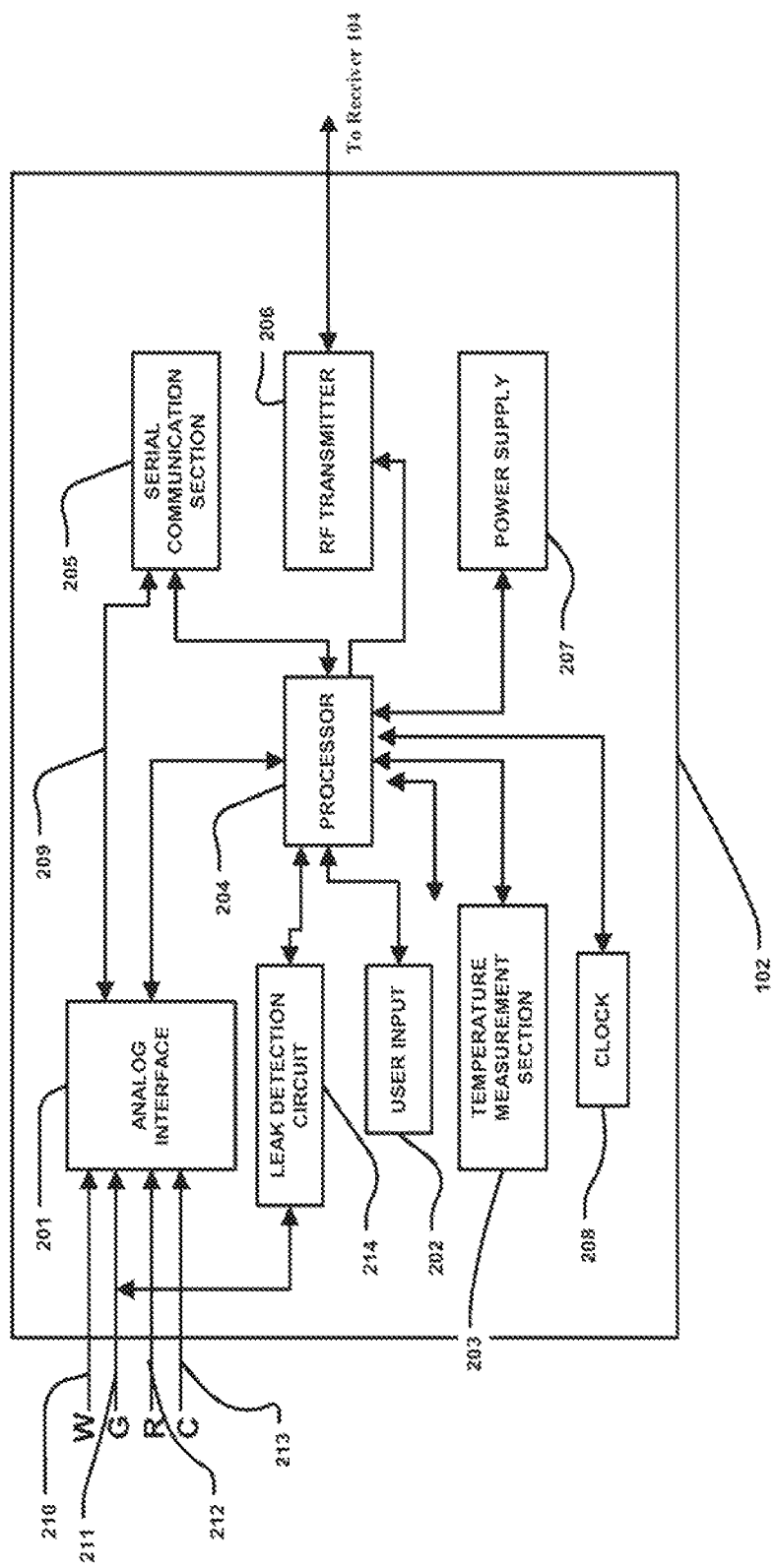
FIG. 2 is a block diagram of the transmitter unit of the data monitoring and management system shown in FIG. 1 in accordance with one embodiment of the present disclosure.

FIG. 2 is a block diagram of the transmitter of the data monitoring and detection system shown in FIG. 1 in accordance with one embodiment of the present disclosure. Referring to the Figure, the transmitter unit 102 in one embodiment includes an analog interface 201 configured to communicate with the sensor 101 (FIG. 1), a user input 202, and a temperature detection section 203, each of which is operatively coupled to a transmitter processor 204 such as a central processing unit (CPU). As can be seen from FIG. 2, there are provided four contacts, three of which are electrodes—work electrode (W) 210, guard contact (G) 211, reference electrode (R) 212, and counter electrode (C) 213, each operatively coupled to the analog interface 201 of the transmitter unit 102 for connection to the sensor unit 101 (FIG. 1). In one embodiment, each of the work electrode (W) 210, guard contact (G) 211, reference electrode (R) 212, and counter electrode (C) 213 may be made using a conductive material that may be applied in any suitable manner, e.g., printed or etched, for example, such as carbon, gold, and the like, which may be printed, or metal foil (e.g., gold) which may be etched.

Further shown in FIG. 2 are a transmitter serial communication section 205 and an RF transmitter 206, each of which is also operatively coupled to the transmitter processor 204. Moreover, a power supply 207 such as a battery is also provided in the transmitter unit 102 to provide the necessary power for the transmitter unit 102. Additionally, as can be seen from the Figure, clock 208 is provided to, among others, supply real time information to the transmitter processor 204.

In one embodiment, a unidirectional input path is established from the sensor 101 (FIG. 1) and/or manufacturing and testing equipment to the analog interface 201 of the transmitter unit 102, while an unidirectional output is established from the output of the RF transmitter 206 of the transmitter unit 102 for transmission to the primary receiver unit 104. In this manner, a data path is shown in FIG. 2 between the aforementioned unidirectional input and output via a dedicated link 209 from the analog interface 201 to serial communication section 205, thereafter to the processor 204, and then to the RF transmitter 206. As such, in one embodiment, via the data path described above, the transmitter unit 102 is configured to transmit to the primary receiver unit 104 (FIG. 1), via the communication link 103 (FIG. 1), processed and encoded data signals received from the sensor 101 (FIG. 1). Additionally, the unidirectional communication data path between the analog interface 201 and the RF transmitter 206 discussed above allows for the configuration of the transmitter unit 102 for operation upon completion of the manufacturing process as well as for direct communication for diagnostic and testing purposes.

As discussed above, the transmitter processor 204 is configured to transmit control signals to the various sections of the transmitter unit 102 during the operation of the transmitter unit 102. In one embodiment, the transmitter processor 204 also includes a memory (not shown) for storing data such as the identification information for the transmitter unit 102, as well as the data signals received from the sensor 101. The stored information may be retrieved and processed for transmission to the primary receiver unit 104 under the control of the transmitter processor 204. Furthermore, the power supply 207 may include a commercially available battery.

The transmitter unit 102 is also configured such that the power supply section 207 is capable of providing power to the transmitter for a predetermined minimum continuous operation time period and also with a predetermined minimum shelf life time period such as, for example, a minimum of about three months of continuous operation after having been stored for about eighteen months in a low-power (non-operating) mode. In one embodiment, this may be achieved by the transmitter processor 204 operating in low power modes in the non-operating state, for example, drawing no more than approximately 1 µA of current. Indeed, in one embodiment, the final step during the manufacturing process of the transmitter unit 102 may place the transmitter unit 102 in the lower power, non-operating state (i.e., post-manufacture sleep mode). In this manner, the shelf life of the transmitter unit 102 may be significantly improved. Moreover, as shown in FIG. 2, while the power supply unit 207 is shown as coupled to the processor 204, and as such, the processor 204 is configured to provide control of the power supply unit 207, it should be noted that within the scope of the present disclosure, the power supply unit 207 is configured to provide the necessary power to each of the components of the transmitter unit 102 shown in FIG. 2.

Referring back to FIG. 2, the power supply section 207 of the transmitter unit 102 in one embodiment may include a rechargeable battery unit that may be recharged by a separate power supply recharging unit (for example, provided in the receiver unit 104) so that the transmitter unit 102 may be powered for a longer period of usage time. Moreover, in one embodiment, the transmitter unit 102 may be configured without a battery in the power supply section 207, in which case the transmitter unit 102 may be configured to receive power from an external power supply source (for example, a battery) as discussed in further detail below.

Referring yet again to FIG. 2, the optional temperature detection section 203 of the transmitter unit 102 is configured to monitor the temperature of the skin near the sensor insertion site. The temperature reading may be used to adjust the analyte readings obtained from the analog interface 201. The RF transmitter 206 of the transmitter unit 102 may be configured for operation in the frequency band of 315 MHz to 322 MHz, for example, in the United States. Further, in one embodiment, the RF transmitter 206 is configured to modulate the carrier frequency by performing Frequency Shift Keying and Manchester encoding. In one embodiment, the data transmission rate is 19,200 symbols per second, with a minimum transmission range for communication with the primary receiver unit 104.

Referring yet again to FIG. 2, also shown is a leak detection circuit 214 coupled to the guard contact (G) 211 and the processor 204 in the transmitter unit 102 of the data monitoring and management system 100. The leak detection circuit 214 in accordance with one embodiment of the present disclosure may be configured to detect leakage current in the sensor 101 to determine whether the measured sensor data is corrupt or whether the measured data from the sensor 101 is accurate.

Additional detailed description of the continuous analyte monitoring system, its various components including the functional descriptions of the transmitter are provided in U.S. Pat. No. 6,175,752 issued Jan. 16, 2001 entitled "Analyte Monitoring Device and Methods of Use", and in application Ser. No. 10/745,878 filed Dec. 26, 2003 entitled "Continuous Glucose Monitoring System and Methods of Use", each assigned to the Assignee of the present application.

Figure 3:
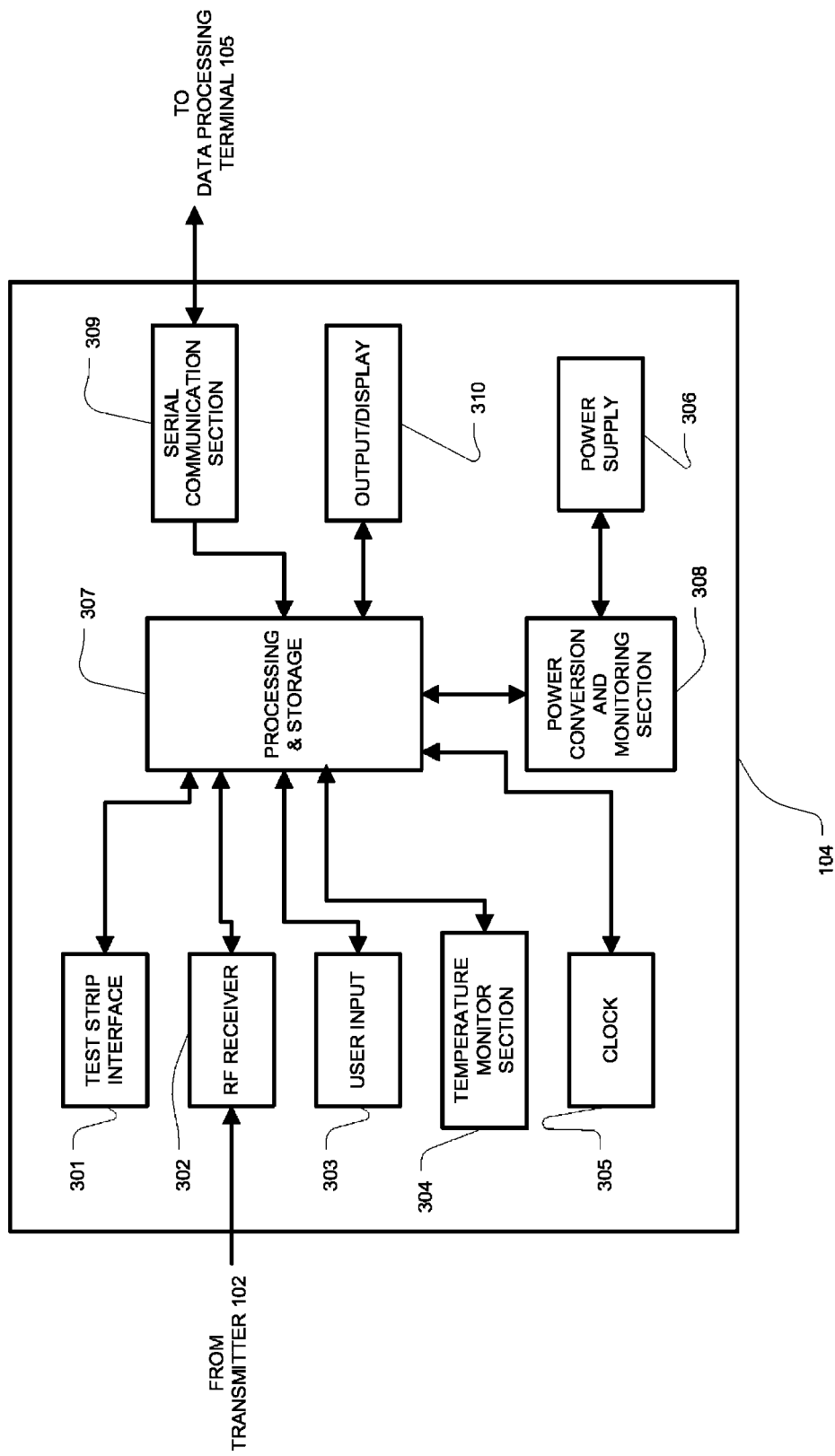
FIG. 3 is a block diagram of the receiver/monitor unit of the data monitoring and management system shown in FIG. 1 in accordance with one embodiment of the present disclosure.

FIG. 3 is a block diagram of the receiver/monitor unit of the data monitoring and management system shown in FIG. 1 in accordance with one embodiment of the present disclosure. Referring to FIG. 3, the primary receiver unit 104 includes a blood glucose test strip interface 301, an RF receiver 302, an input 303, a temperature detection section 304, and a clock 305, each of which is operatively coupled to a receiver processor 307. As can be further seen from the Figure, the primary receiver unit 104 also includes a power supply 306 operatively coupled to a power conversion and monitoring section 308. Further, the power conversion and monitoring section 308 is also coupled to the receiver processor 307. Moreover, also shown are a receiver serial communication section 309, and an output 310, each operatively coupled to the receiver processor 307.

In one embodiment, the test strip interface 301 includes a glucose level testing portion to receive a manual insertion of a glucose test strip, and thereby determine and display the glucose level of the test strip on the output 310 of the primary receiver unit 104. This manual testing of glucose can be used to calibrate sensor 101. The RF receiver 302 is configured to communicate, via the communication link 103 (FIG. 1) with the RF transmitter 206 of the transmitter unit 102, to receive encoded data signals from the transmitter unit 102 for, among others, signal mixing, demodulation, and other data processing. The input 303 of the primary receiver unit 104 is configured to allow the user to enter information into the primary receiver unit 104 as needed. In one aspect, the input 303 may include one or more keys of a keypad, a touch-sensitive screen, or a voice-activated input command unit. The temperature detection section 304 is configured to provide temperature information of the primary receiver unit 104 to the receiver processor 307, while the clock 305 provides, among others, real time information to the receiver processor 307.

Each of the various components of the primary receiver unit 104 shown in FIG. 3 is powered by the power supply 306 which, in one embodiment, includes a battery. Furthermore, the power conversion and monitoring section 308 is configured to monitor the power usage by the various components in the primary receiver unit 104 for effective power management and to alert the user, for example, in the event of power usage which renders the primary receiver unit 104 in sub-optimal operating conditions. An example of such sub-optimal operating condition may include, for example, operating the vibration output mode (as discussed below) for a period of time thus substantially draining the power supply 306 while the processor 307 (thus, the primary receiver unit 104) is turned on. Moreover, the power conversion and monitoring section 308 may additionally be configured to include a reverse polarity protection circuit such as a field effect transistor (FET) configured as a battery activated switch.

The serial communication section 309 in the primary receiver unit 104 is configured to provide a bi-directional communication path from the testing and/or manufacturing equipment for, among others, initialization, testing, and configuration of the primary receiver unit 104. Serial communication section 309 can also be used to upload data to a computer, such as time-stamped blood glucose data. The communication link with an external device (not shown) can be made, for example, by cable, infrared (IR) or RF link. The output 310 of the primary receiver unit 104 is configured to provide, among others, a graphical user interface (GUI) such as a liquid crystal display (LCD) for displaying information. Additionally, the output 310 may also include an integrated speaker for outputting audible signals as well as to provide vibration output as commonly found in handheld electronic devices, such as mobile telephones presently available. In a further embodiment, the primary receiver unit 104 also includes an electro-luminescent lamp configured to provide backlighting to the output 310 for output visual display in dark ambient surroundings.

Referring back to FIG. 3, the primary receiver unit 104 in one embodiment may also include a storage section such as a programmable, non-volatile memory device as part of the processor 307, or provided separately in the primary receiver unit 104, operatively coupled to the processor 307. The processor 307 may be configured to perform Manchester decoding as well as error detection and correction upon the encoded data signals received from the transmitter unit 102 via the communication link 103.

Figure 4:
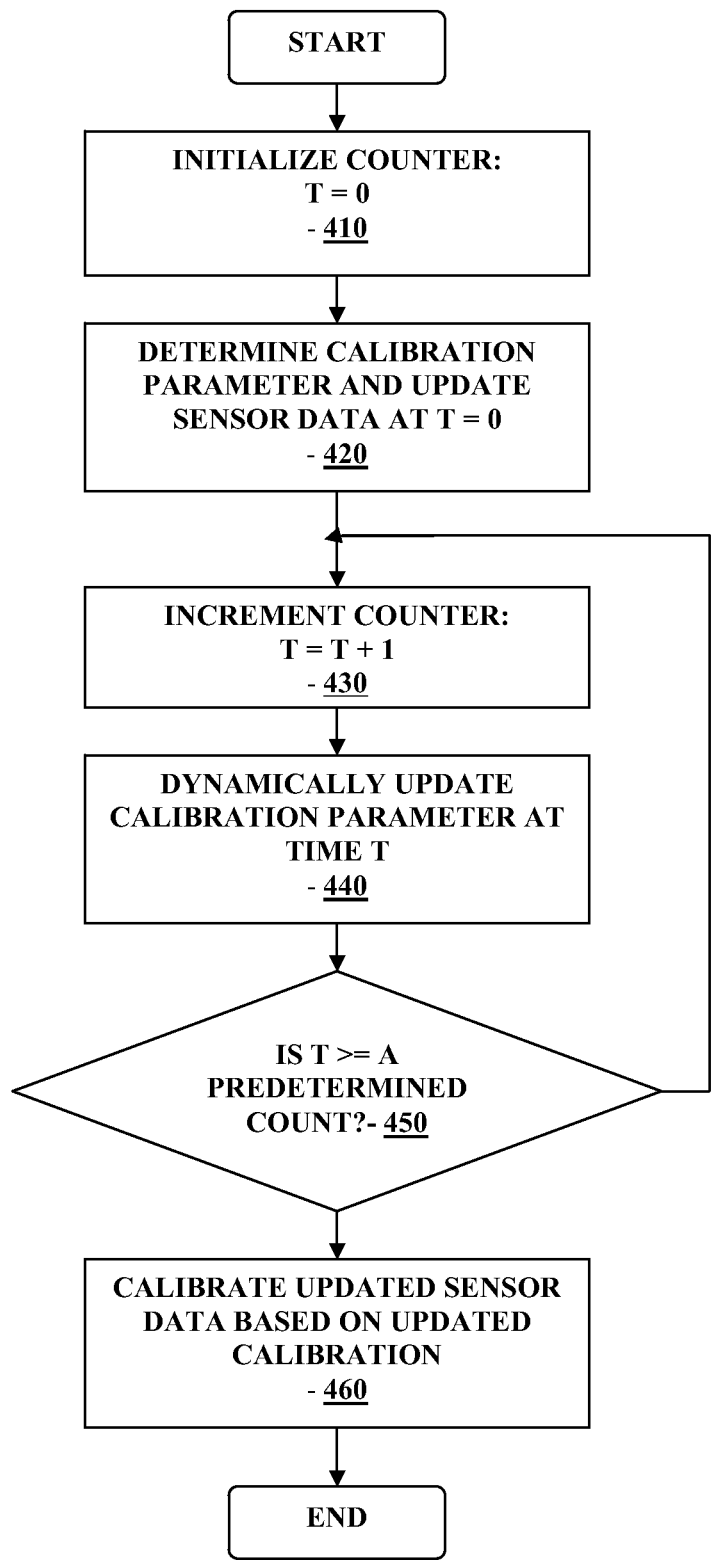
FIG. 4 is a flowchart illustrating an overall dynamically updating calibration in accordance with one embodiment of the present disclosure.

FIG. 4 is a flowchart illustrating an overall dynamically updating calibration in accordance with various embodiments of the present disclosure. Referring to FIG. 4, a counter such as a calibration counter is triggered to perform calibration of the monitored data such as the analyte data received from the transmitter unit 102 (FIG. 1). In one aspect, the calibration may be performed on calibrated data, or on the uncalibrated data, for example, on the analyte data received prior to the initial calibration performed. In one embodiment, the calibration counter may include a timer or a clock which may be configured to prompt the user or the patient to initiate the acquisition of reference data (e.g., blood glucose reference data, e.g., obtained using a test strip/meter system) at predetermined time intervals. When the calibration counter is initially triggered, the time counter T is initialized to zero (0). Thereafter, a calibration parameter is determined based on, for example, the acquired reference data and the monitored sensor data at time T=0. Moreover, in one embodiment, the monitored sensor data may be updated based on the calibration parameter. In one embodiment, the calibration parameter may include a sensor sensitivity value associated with the analyte sensor 101 (FIG. 1) configured to monitor the analyte levels of the patient.

As described in further detail below, for example, in conjunction with FIG. 5, in particular embodiments, during the initial calibration stage at T=0, a reference glucose value is determined, for example, such as a capillary blood glucose value using a blood glucose determination system such as FreeStyle® blood glucose monitoring system or Precision® blood glucose monitoring system available from Abbott Diabetes Care, Inc., Alameda, Calif. In certain embodiments, an analyte meter may be integrated into the receiver unit. In addition, the monitored sensor data at or near the calibration time (T=0) is retrieved which may include the monitored sensor data at time T=T−1, at time T=T+1, or any other suitable time period (for example, from the processing and storage unit 307 (FIG. 3) of the receiver unit 104 (FIG. 1)).

More specifically, in one embodiment, the monitored sensor data at the calibration time (T=0) may include one or more monitored sensor data in addition to the monitored sensor data point at the calibration time (T=0). That is, in one embodiment, the monitored sensor data at the calibration time (T=0) may include all monitored sensor data available for retrieval from the receiver unit 104 (FIG. 1) at the calibration time (T=0). For example, to reduce the contribution of noise in the measured sensor data, an average of the two most recent sensor data may be associated with the monitored sensor data at the calibration time (T=0).

The monitored sensor data at a predetermined time may include, in particular embodiments, an estimate of the sensor data at the predetermined time as determined by the one or more filters which may be configured to use the monitored sensor data up to and including the data point at the predetermined time (for example, up to the data point at calibration time (T=0)). In one embodiment, one or more filters such as a finite impulse response (FIR) filter may be used to determine the best estimate at a predetermined time using a finite window of monitored sensor data up to the current or most recent monitored sensor data point.

Referring back to FIG. 4, after determining the calibration parameter and updating the monitored data at the calibration time (T=0), the counter is incremented by one (1), and dynamic, real-time update of the calibration parameter is performed. In one embodiment, the counter may be configured to increment by one with each reception of sensor data from the transmitter unit 102 (FIG. 1). After dynamically updating the calibration parameter at the subsequent incremented time (T=1), it is determined whether the counter has reached a predetermined count (for example, set at seven (7)). If it is determined that the counter has not reached the predetermined count, then the routine in one embodiment returns to step 430 where the counter is incremented by one (1) and the dynamically updating calibration parameter and monitored sensor data is performed for monitored data at the second subsequent incremented time (T=2).

On the other hand, if it is determined that the counter has reached the predetermined count, then in one embodiment, subsequent monitored sensor data may be updated based on the dynamically updated calibration parameter and/or updated monitored sensor data. Thereafter, in particular embodiments, it is determined whether further or subsequent lag correction will likely not yield more accurate monitored data values (or with less errors). Therefore, in one embodiment, the routine terminates and awaits for the subsequent calibration time, for example, to repeat the processes described above in conjunction with FIG. 4. When a procedure such as described in FIG. 4 has been successfully completed, routines such as determining lag time constant based on calibrated sensor data 740 (FIG. 7) may be updated in order to obtain a better estimate.

In this manner, there are provided methods and system for dynamically, and in particular embodiments, in real-time, obtaining reference data at a first predetermined time, receiving measured data prior to and including (or near) the first predetermined time, calculating a first calibration parameter (or parameters) using the data, calibrating the measured data based on the calibration parameter, receiving measured data at a second predetermined time, updating the calibration parameter based on all of the previous data and the newly received measured data, calibrating the newly received measured data based on the updated calibration parameter, and repeating a number of times the process of receiving new measurement data, updating the calibration parameter, calibrating the newly received measurement data, and calibrating any newly received measurement data with the fully updated calibration parameter.

A method in a further embodiment may include performing lag compensation on the measured data that is used to update the calibration parameter. Lag compensation may optionally be performed on the measured data that is calibrated or on uncalibrated data. A method in a further embodiment includes filtering the measured data that is used to update the calibration parameter.

Figure 5:
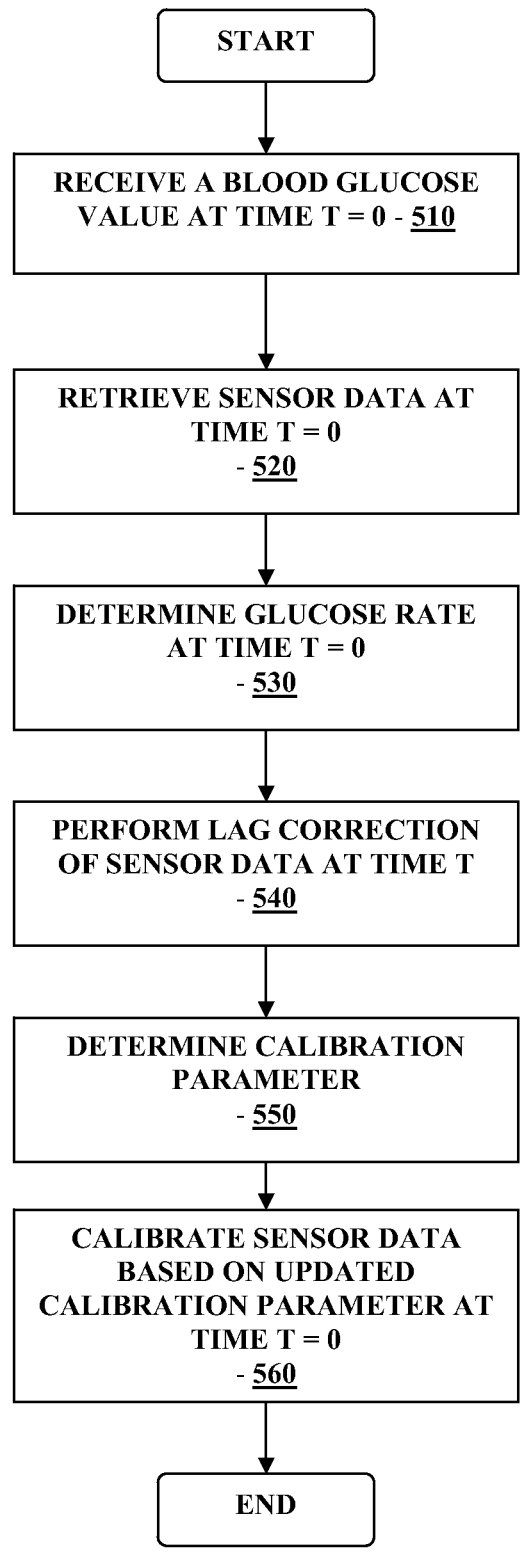
FIG. 5 is a flowchart illustrating the lag correction and calibration routine of the overall dynamically updating calibration shown in FIG. 4 in accordance with one embodiment of the present disclosure.

FIG. 5 is a flowchart illustrating the lag correction and calibration routine of the overall dynamically updating calibration shown in FIG. 4 in accordance with one embodiment of the present disclosure. Referring to FIG. 5, the determination of calibration parameter and updating the monitored analyte level at the calibration time (T=0) is described in further detail. More specifically, in one embodiment, a capillary blood glucose value is determined at the calibration time (T=0), and the monitored analyte value at the calibration time is retrieved from the receiver unit 104 of the monitoring system 100 (FIG. 1).

Thereafter, a rate of change of the monitored data at the calibration time (T=0) is determined. In one embodiment, the rate of change of the monitored data at the calibration time (T=0) may be determined using one or more filters including, but not limited to infinite impulse response (IIR) filter, finite impulse response (FIR) filter, backward and/or forward smoothing techniques (e.g., Kalman filtering technique), or any other equivalent one or more causal filters that balance signal noise reduction with lag correction.

Upon determining the rate of change of the monitored data at the calibration time (T=0), the monitored data at the calibration time (T=0) is updated. In one embodiment, the updated monitored sensor data may include lag corrected monitored data at the calibration time (T=0). Optionally, the lag correction for the monitored data at the calibration time (T=0) may be skipped and not performed. In one embodiment, the lag corrected monitored data at the calibration time (T=0) may be determined by applying the determined rate of change of the monitored data at the calibration time (T=0) to a predetermined constant value. In one embodiment, the predetermined constant value may include, a predetermined time constant.

For example, in one embodiment, the predetermined time constant may include a fixed time constant in the range of approximately four to fifteen minutes, and which may be associated with the one or more of the patient physiological profile, one or more attributes associated with the monitoring system 100 (including, for example but not limited to, the characteristics of the analyte sensor 101). In a further aspect, the predetermined time constant may vary based on one or more factors including, for example, but not limited to the timing and amount of food intake by the patient, exogenous insulin intake, physical activities by the patient such as exercise, or any other factors that may affect the time constant, and which may be empirically determined.

Referring again to FIG. 5, the calibration parameter (for example, the sensitivity of the analyte sensor 101 FIG. 1), may be determined for example, in one embodiment, by determining the ratio of the monitored data (optionally lag corrected) at the calibration time (T=0) and the reference data obtained using, for example, the blood glucose meter as described above. In one embodiment, the calibration parameter may be determined by dividing the monitored data at the calibration time (T=0) by the reference data such as the capillary blood glucose value at the calibration time (T=0).

Thereafter, in one embodiment, the calibrated and updated monitored sensor data at the calibration time (T=0) is determined based upon the monitored data (optionally lag corrected) and the calibration parameter as determined above. For example, in one embodiment, the calibrated and updated monitored sensor data at the calibration time (T=0) may be determined by dividing the lag corrected monitored data at calibration time (T=0) by the determined calibration parameter.

Figure 6:
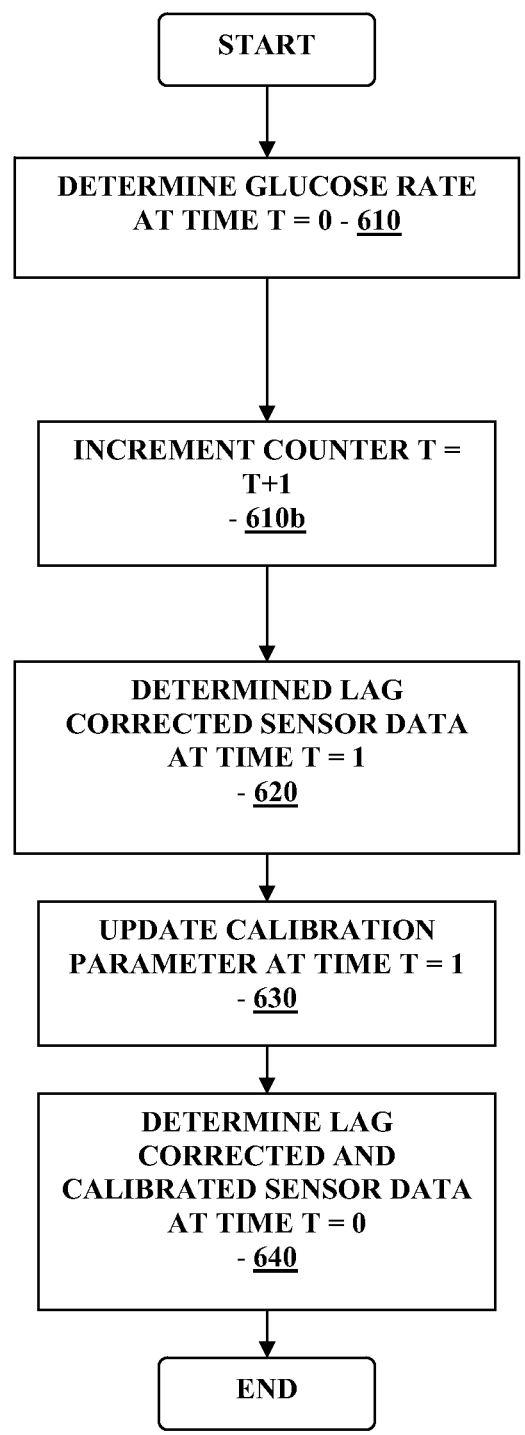
FIG. 6 is a flowchart illustrating the lag correction and dynamically updating calibration routine of the overall dynamically updating calibration shown in FIG. 4 in accordance with one embodiment of the present disclosure.

FIG. 6 is a flowchart illustrating the lag correction and dynamically updating calibration routine of the overall dynamically updating calibration shown in FIG. 4 in accordance with one embodiment of the present disclosure. Referring to FIGS. 4 and 6, with the counter incremented by one (see step 430 of FIG. 4), the analyte value at the subsequent incremented time (T=1) is retrieved from, for example, the processing and storage unit 307 (FIG. 3) of the receiver unit 104. In particular, in one embodiment, the rate of change of the monitored data at the calibration time (T=0) is updated based on the monitored data value at the subsequent incremented time (T=1). In other words, the process starts with the determination of glucose rate of change at calibration time (T=0) 610 in FIG. 6. At the next time increment, this value is revised using the monitored data values at calibration time (T=0) and prior data and at the subsequent incremented time (T=1) (see 620 and 630 of FIG. 6), the rate of change of the monitored data at the calibration time (T=0) may be estimated with an improved accuracy at T=1 (see 640 of FIG. 6). Again, in one embodiment, the rate of change may be determined based on one or more of, but not limited to, infinite impulse response (IIR) filter, finite impulse response (FIR) filter, backward and/or forward smoothing techniques (e.g., Kalman filtering technique), or any other equivalent filtering or smoothing techniques.

With the updated rate of change at the calibration time (T=0) determined, monitored data (optionally lag corrected) at calibration time (T=0) is updated. That is, in one embodiment, the lag corrected sensor data at the calibration time (T=0) is updated based on the prior lag corrected and calibrated data at calibration time (T=0), and in conjunction with the predetermined constant (for example, the predetermined time constant discussed above), and the updated rate of change of the monitored data at the calibration time (T=0). For example, in one embodiment, the lag corrected monitored data at the calibration time (T=0) is updated or determined by taking the sum of the lag corrected and calibration sensor value at calibration time (T=0) as determined above, with the updated rate of change of monitored data at calibration time (T=0) multiplied by the predetermined constant. In other words, in one embodiment, the updated rate of change of the monitored data at calibration time (T=0) may be multiplied by the predetermined constant, and thereafter, the resulting value is added to the lag corrected and calibrated monitored data at the calibration time (T=0) previously determined (see for example, step 420).

Referring again to FIG. 6, after determining the updated lag corrected monitored data at calibration time (T=0) based on monitored data at the subsequent incremented time (T=1) as described above, in one embodiment, the calibration parameter (for example, the sensitivity of the sensor 101 (FIG. 1)) is updated based on the updated lag corrected monitored data at calibration time (T=0) described above. In particular, in one embodiment, the calibration parameter may be updated by determining the ratio of the updated lag corrected monitored data at calibration time (T=0) and the reference value (for example, the capillary blood glucose value) determined at calibration time (T=0).

After updating the calibration parameter as described above, in one embodiment, the lag corrected and calibrated monitored data at the subsequent incremented time (T=1) is determined based on the updated calibration parameter value. For example, in one embodiment, the monitored sensor data at the subsequent incremented time (T=1) in one embodiment may be divided by the updated sensitivity to determine the dynamically lag corrected and calibrated monitored sensor data at the subsequent incremented time (T=1).

In another embodiment, the dynamically lag corrected and calibrated monitored sensor data at the subsequent incremented time (T=1) may be determined based on the updated calibration parameter and the dynamically lag corrected monitored sensor data at the subsequent incremented time (T=1). In this case, the dynamically updated sensor data at the subsequent incremented time (T=1) in one embodiment may be determined by calculating the rate of change of the monitored data at the subsequent incremented time (T=1) using similar filtering techniques as described above, and applying the predetermined constant (for example, the predetermined time constant discussed above), the result of which is then added to the detected or monitored data at the subsequent incremented time (T=1). In other words, in one embodiment, the calculated rate of change of the monitored data at the subsequent incremented time (T=1) is multiplied by the predetermined time constant, and the resulting value is added to the monitored data value at the subsequent incremented time (T=1). This sum in one embodiment represents the dynamically updated monitored sensor data at the subsequent incremented time (T=1).

In this manner, in one embodiment, lag correction of analyte sensor data may be pseudo-retrospectively (or substantially in real time) updated using the monitored analyte data stream substantially continuously detected by the sensor 101 (FIG. 1) with the dynamic updating of the calibration parameter. Thus, in one aspect, lag error or error due to lag compensation may be overcome by, for example, updating the sensor sensitivity retrospectively with each value of the detected or monitored analyte levels. Accordingly, in one embodiment, calibration inaccuracies due to change (for example, rapid acceleration) of analyte levels after performing discrete calibration may be mitigated by updating the calibration routine taking into consideration the near immediate post calibration analyte sensor data to obtain a more reliable and accurate value associated with the rate of change of the monitored analyte levels. In one embodiment, the overall system accuracy of the monitored and detected analyte values may be improved.

Figure 7:
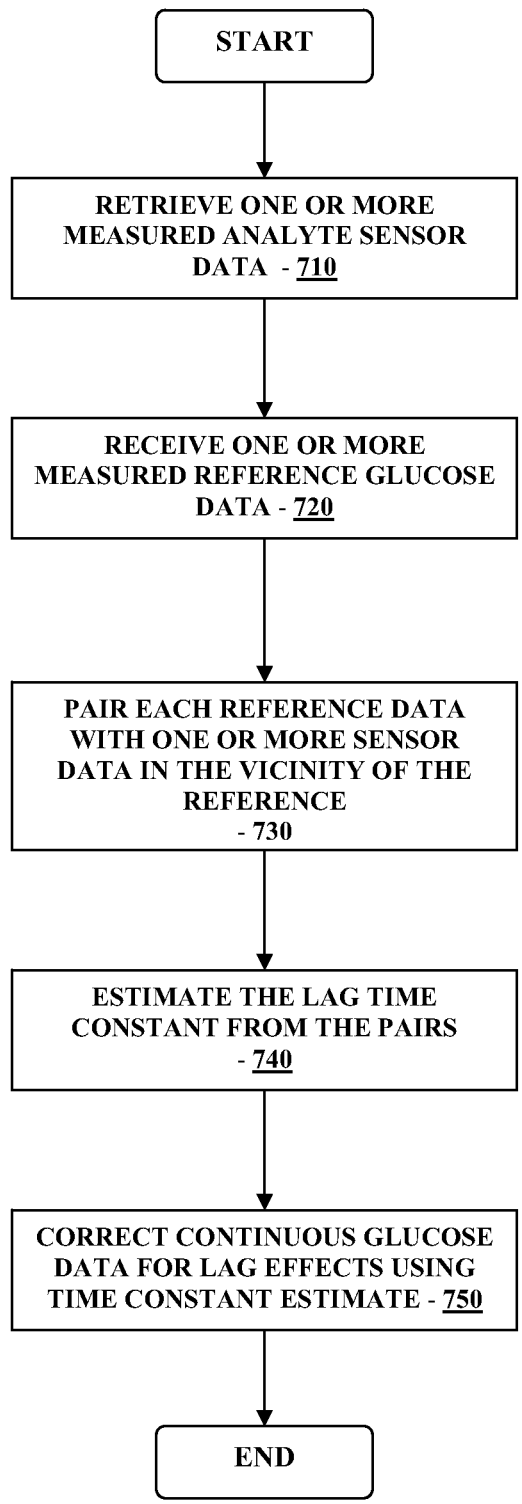
FIG. 7 is a flowchart illustrating a method for estimating the lag time constant from sensor analyte data and reference measurements in accordance with one embodiment of the present disclosure.

FIG. 7 is a flowchart illustrating a method for estimating the lag time constant from sensor analyte data and reference measurements in accordance with one embodiment of the present disclosure. This method can be employed in real-time or offline, or components of the method may be one or the other. Referring to FIG. 7, measured analyte sensor data for example, from a transcutaneously positioned analyte sensor may be obtained and/or retrieved from a memory or storage device operatively coupled to the analyte sensor (710). Thereafter, a reference glucose data measurement is performed and received, for example, from a blood glucose meter (720). Each of the reference glucose data is paired with one or more measured analyte sensor data in the same time vicinity as the reference data (730). That is, the pairing may be to select a single analyte sensor data closest in time to the time of the reference data. Alternatively, the pairing could be a number of analyte sensor data occurring before and after the reference data. Alternatively, the pairing could be between a value that is the result of a calculation using a number of analyte sensor data occurring before and after the reference data; the calculation could be an average or some other appropriate form of filtering.

Referring back to FIG. 7, thereafter, these pairs are used to estimate the lag time constant (740). This estimate could be performed using standard system identification techniques.

Figure 8:
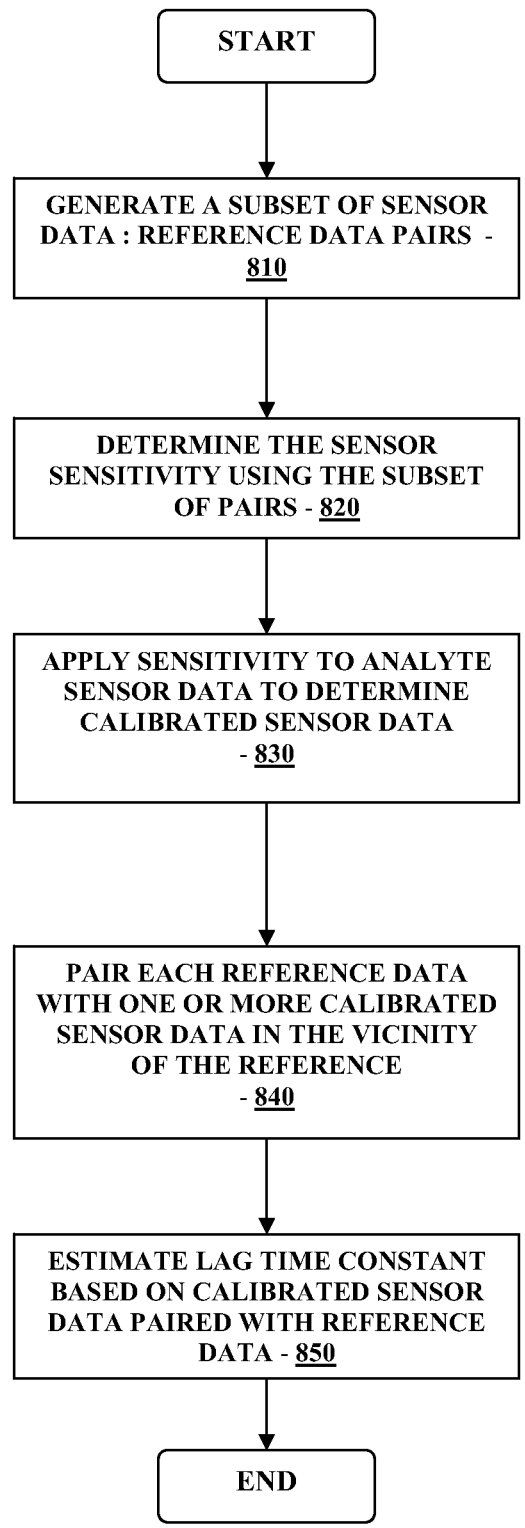
FIG. 8 is a flowchart illustrating lag time constant compensated analyte sensor data in accordance with one embodiment of the present disclosure.

For instance, a 2 or more dimensional least squares technique could be used to estimate the time constant, along with the sensor sensitivity. The preferred embodiment for estimating the time constant separates the estimation of the sensitivity from the estimation of the lag time constant, and is illustrated in FIG. 8, and described later.

Once the estimate of the lag time constant is determined, it may be used to correct the sensor data for lag effects (750). In one aspect, calibration for lag effects may be corrected. In another aspect, each calibrated sensor data may be corrected for lag effects as described below.

Given a calibrated sensor providing a continuous stream of interstitial glucose $G_i$, lag correction routine used to improve calibration may also be used to provide a blood glucose estimate $G_b$. For example, consider a simple continuous time domain model of blood glucose-to-interstitial glucose dynamics:

$$\tau \dot{G}_i(t) = -G_i(t) + G_b(t)$$

where $\tau$ is the time constant, and $\dot{G}_i$ is the rate of change of glucose level $G_i$. Given that glucose $G_i$ is available or determined by another module made possible by the latest calibration procedure, the rate of change of the glucose level $\dot{G}_i$ may be determined in one or more retrospectively or in real-time. The time constant $\tau$ is available or computed by another module.

One real-time example to obtain a sampled data estimate of the rate of change $\dot{G}_i$ at any time n is to use the average first difference of the past N sampled $G_i$ data:

$$\hat{\dot{G}}_i(n) \approx \frac{\sum_{n=1}^{N} G_i(n) - G_i(n-1)}{N T_s}$$

where $T_s$ is the sample time or the time interval between the sampled values of $G_i(n)$. The notation $\hat{\dot{G}}_i$ signifies that it is an estimate for $\dot{G}_i$. Other approaches to compute $\dot{G}_i$ include any other Finite Impulse Response (FIR) filters, Infinite Impulse Response (IIR) filters, Wiener filter, and Kalman filter.

Given these available and/or computed values, blood glucose estimate $G_b$ can be computed by rearranging the blood glucose-to-interstitial glucose model in the following manner:

$$\hat{G}_b(n) = G_i(n) + \tau \hat{\dot{G}}_i(n)$$

where n is any time instance. Note that for improved noise rejection, the first term on the right hand side, $G_i(n)$, may be replaced by a filtered version. The filter can take any eligible forms such as the FIR filter, IIR filter, Wiener filter, or the Kalman filter.

In one embodiment, steps 730 and 740 are performed as a batch process. For instance, the receiver unit 104, may perform the routines described at steps 730 and 740 periodically or continuously, after each reference measurement, with a batch of data saved on the receiver unit 104. After each batch process, the lag time constant may be updated and used for subsequent real-time lag correction processes. Another embodiment may include the batch process to be performed external to the receiver unit in a computer terminal, for example. After the time constant is estimated, it may be downloaded or transmitted to the receiver unit to be used in subsequent real time lag correction processes.

In a further aspect, the routine illustrated in FIG. 7 may be performed retrospectively, for example, using a computer or server terminal. This may be used in applications where lag correction operations may be performed retrospectively.

FIG. 8 illustrates estimation of the lag time constant from the pairs 740 of FIG. 7 in one embodiment. The generation of a subset of pairs (810) may include generating a subset from pairs associated with sensor data absolute rate of change that is below a predetermined threshold. An example of the predetermined threshold includes 0.1 mg/dL/minute. An alternative predetermined threshold may be 6% change in the glucose estimate per minute. That is, the lag effects may be minimized if the rate of change is relatively low, and the subsequent estimation of the sensitivity (820) may be minimally affected by lag. Additionally, the included pairs may form a cluster of data in time. Other criteria for creating a subset of pairs may include a) data from a single sensor, b) data from a single subject, c) data from groups of patients or users, d) data associated with any particular conditions, such as data where all glucose is above some value, e) data that meets certain data quality conditions.

In the case where the criteria for generating a subset of pairs includes determining the glucose rate of change is below a predetermined glucose rate of change threshold, then the measured sensor data may be converted to preliminary glucose estimates using a preliminary sensitivity. The preliminary sensitivity may be determined by a variety of ways, including: the use of a nominal sensitivity assigned at the factor for a particular lot of sensors, the use of the median of the sensitivities calculated for each pair, or another suitable means. In the case where the criteria includes a percentage of signal change, then the determination of the preliminary sensitivity is not needed.

The pair subset criterion in one aspect may include a condition that the data be from one sensor. In this embodiment, the sensitivity is estimated (820) for one sensor and the lag time constant is subsequently estimated (830-850). The receiver unit may subsequently use this time constant in real time to correct calibration and glucose calculations for lag effects. Further, this process may be repeated for multiple sensors, and the resulting multiple lag time constant estimates could be combined to create a single estimate used for lag correction. A simple combination calculation may include an average; other combination calculations, such as an FIR filter or a median or a time weighted average.

The pair subset criterion may alternatively include that the data must be from one patient, over multiple sensors. This subset may be further segregated by sensor when determining sensor sensitivity (820) and applying the determined sensitivity to the analyte sensor data (830).

Referring back to FIG. 8, the sensitivity of a subset of pairs is determined (820). In one aspect, a ratio for each reference data and associated sensor data (or value representing a combination of sensor data) are determined, and the median from this set of ratios is determined.

The sensitivity estimated is applied to the analyte sensor data (830) to generate the calibrated sensor data. Specifically, each sensor data point is divided by the sensitivity ratio to convert the sensor data from its native measurement units into glucose units. If the pair subsets (810) include data from multiple sensors, then the sensitivity estimated for each sensor is applied to the sensor data associated with that sensor.

Referring still to FIG. 8, the calibrated sensor data is paired with reference data (840). In a further aspect, another pair subset may be created to only include pairs where the glucose absolute rate of change based on the sensor exceeded a predetermined threshold, for example 0.75 mg/dL. In this case, the pairs associated with low glucose rate of change may be minimally informative to the lag time constant estimation.

This may not be necessary to produce a result, but may be useful to reduce the amount of computation needed if this is desirable.

In step 850, the pairs of calibrated sensor data and reference data are used to estimate the lag time constant. One embodiment of the time constant calculation is to assume that the interstitial fluid glucose level is connected to the blood glucose level by a simple first order differential expression:

$$\tau \frac{dI_{NAV}}{dt} = -I_{NAV} + SG_{REF}.$$

Here, $\tau$, is the time constant, $I_{NAV}$ is the sensor data measurement, S is the ratio of sensor current to blood glucose concentration (sensitivity), and $G_{REF}$ is a blood glucose reference measurement. This equation may be solved for $\tau$ if the values of the other quantities can be estimated. One approach for estimation of the sensor data measurement and its time rate of change may require filtering of the signal in order to reduce the effect of high frequency noise. In one aspect, the sensor data may be fit in a time interval around the reference point, $G_{REF}$, to a low order polynomial via the least squares algorithm. Another embodiment is to use a causal or non-causal low-pass filter.

If more than one reference point is available, then there will be multiple values of the time constant $\tau$, and in which case, a least squares approach may be applied Accordingly, the identification of the sensitivity parameter may be isolated from that of the lag parameter. Moreover, in one aspect, data exclusion may be in the routine illustrated in FIG. 8. In one embodiment, a paired point exclusion may be added just after calibrated sensor data is paired with reference data, where the exclusion criteria may be a constraint appropriate for improving the estimate of lag. For instance, if the lag time constant at high glucose values is desirable to determine, then a step could be added to exclude pairs associated with a reference below a predetermined glucose threshold.

In this manner, the time lag constant determination associated with an analyte sensor for lag correction may be implemented in a real time monitoring system such as one aspect of the analyte monitoring system 100, or alternatively, may be used as an analysis too, for example, by a patient, a physician or a health care provider to improve the treatment of the patient based on improved physiological data associated with the patient with minimal errors.

Indeed, in one aspect, lag compensation of analyte sensor measurements may be tuned or adjusted to the particular analyte sensor in use by the patient or the user, resulting in improved accuracy of the overall analyte monitoring system 100.

It is to be noted that, each step or routine associated each of the flowcharts illustrating the various embodiments of the present disclosure as shown in FIG. 4-8 do not have to be performed in the order shown in the Figures, unless described otherwise, and within the scope of the present disclosure, one or more step or routine in one or more figures described above may be performed or executed in an order different from the order shown in the respective figures.

Referring to the Figures above, in particular embodiments, the lag correction and calibration and updating of monitored sensor data may be performed by one or more processing units of the one or more receiver unit (104, 106) the transmitter unit 102 or the data processing terminal/infusion section 105. In addition, the one or more of the transmitter unit 102, the primary receiver unit 104, secondary receiver unit 106, or the data processing terminal/infusion section 105 may also incorporate a blood glucose meter functionality, such that, the housing of the respective one or more of the transmitter unit 102, the primary receiver unit 104, secondary receiver unit 106, or the data processing terminal/infusion section 105 may include a test strip port configured to receive a blood sample for determining one or more blood glucose levels of the patient.

In a further embodiment, the one or more of the transmitter unit 102, the primary receiver unit 104, secondary receiver unit 106, or the data processing terminal/infusion section 105 may be configured to receive the blood glucose value wirelessly over a communication link from, for example, a glucose meter. In still a further embodiment, the user or patient manipulating or using the analyte monitoring system 100 (FIG. 1) may manually input the blood glucose value using, for example, a user interface (for example, a keyboard, keypad, and the like) incorporated in the one or more of the transmitter unit 102, the primary receiver unit 104, secondary receiver unit 106, or the data processing terminal/infusion section 105.

A computer implemented method in accordance with one embodiment includes determining a rate of change of an analyte level monitored by an analyte sensor below a predetermined threshold, calibrating analyte data associated with the monitored analyte level received from analyte sensor based on a reference measurement, determining a time lag constant associated with the calibrated analyte data, and performing lag correction of the calibrated analyte data based on the determined time lag constant.

The method may include outputting the lag corrected calibrated analyte data.

In one aspect, the reference measurement may include a blood glucose measurement.

The reference measurement may be obtained within a predetermined time period relative to the monitored analyte level, where the predetermined time period may be less than approximately 30 minutes or greater than approximately 30 minutes, or any other suitable time range.

In one aspect, calibrating the analyte data may include determining a sensitivity value associated with the analyte sensor, where the sensitivity value may include a ratio of the analyte data and the corresponding reference measurement.

The analyte level may include glucose level.

In a further aspect, determining the rate of change may include determining a rate of increase or a rate of decrease of the monitored analyte level for a predefined time period.

An apparatus in accordance with one embodiment may include one or more processing units, and a memory for storing instructions which, when executed by the one or more processors, causes the one or more processing units to determine a rate of change of an analyte level monitored by an analyte sensor below a predetermined threshold, calibrate analyte data associated with the monitored analyte level received from analyte sensor based on a reference measurement, determine a time lag constant associated with the calibrated analyte data, and perform lag correction of the calibrated analyte data based on the determined time lag constant.

The memory may be further configured for storing instructions which, when executed by the one or more processing units, causes the one or more processing units to output the lag corrected calibrated analyte data.

In a further aspect, the apparatus may include a communication module operatively coupled to the one or more processing units, the communication module configured to receive the reference measurement within a predetermined time period relative to the monitored analyte level, where the predetermined time period may be less than approximately 30 minutes or greater than approximately 30 minutes, or any other suitable time period.

In a further aspect, the memory may be further configured for storing instructions which, when executed by the one or more processing units, causes the one or more processing units to determine a sensitivity value associated with the analyte sensor, where the sensitivity value may include a ratio of the analyte data and the corresponding reference measurement.

The memory may be further configured for storing instructions which, when executed by the one or more processing units, causes the one or more processing units to determine the rate of change based on determining a rate of increase or a rate of decrease of the monitored analyte level for a predefined time period.

A physiological monitoring device in still another aspect may include means for determining a rate of change of an analyte level monitored by an analyte sensor below a predetermined threshold, means for calibrating analyte data associated with the monitored analyte level received from analyte sensor based on a reference measurement, means for determining a time lag constant associated with the calibrated analyte data, and means for performing lag correction of the calibrated analyte data based on the determined time lag constant.

A method in accordance with one embodiment of the present disclosure includes obtaining a reference data point at a first predetermined time, receiving a first data at the first predetermined time, calibrating the first data based on the reference data point, receiving a second data at a second predetermined time, updating the calibrated first data based on the second data, and calibrating the second data.

The reference data point may include a blood glucose value.

The first predetermined time may include a calibration time associated with the calibration of one or more of the first data or the second data.

The first data and the second data may include a respective one of a monitored analyte value.

In one embodiment, calibrating the first data may include determining a first rate of change of the first data at the first predetermined time, and performing a first lag compensation of the first data based on the first rate of change to generate a first lag compensated first data. In a further embodiment, calibrating the first data may include determining a first calibration parameter associated with the first data based on the reference data point and the first lag compensated first data, and generating a calibrated first data based on the first calibration parameter and the first lag compensated first data.

Updating the calibrated first data in one embodiment may include determining a second rate of change of the first data at the first predetermined time based on the second data, and performing a second lag compensation of the first data based on the second rate of change of the first data to generate a second lag compensated first data.

Also, calibrating the second data may include determining a second calibration parameter associated with the first data based on the reference data point and the second lag compensated first data, and generating a calibrated second data based on the second calibration parameter and the second lag compensated first data.

A method in accordance with another embodiment may include determining a calibration parameter associated with a detected analyte value, calibrating the analyte value based on the calibration parameter, and dynamically updating the calibration parameter.

The method in another aspect may include calibrating a second detected analyte value based on the dynamically updated calibration parameter.

Further, dynamically updating the calibration parameter may also include determining a rate of change of the detected analyte value, and generating a lag compensated analyte value based on the rate of change.

In addition, calibrating the analyte value may further include determining a sensitivity associated with the detected analyte value, and applying the sensitivity to the lag compensated analyte value.

Moreover, in still another embodiment, dynamically updating the calibration parameter may include updating the rate of change of the detected analyte value, and updating the lag compensated analyte value, where updating the rate of change may include determining the rate of change of the detected analyte value between a first predetermined time and a second predetermined time.

In still another embodiment, calibrating the analyte value may include detecting a calibration data, determining a sensitivity based on the calibration data and the lag compensated analyte value, and generating a lag compensated and calibrated analyte value.

An apparatus in accordance with another embodiment may include one or more processing units, and a memory for storing instructions which, when executed by the one or more processors, causes the one or more processing units to obtain a reference data point at a first predetermined time, receive a first data at the first predetermined time, calibrate the first data based on the reference data point; receive a second data at a second predetermined time; update the calibrated first data based on the second data; and calibrate the second data.

The memory in another aspect may be configured for storing instructions which, when executed by the one or more processing units, causes the one or more processing units to determine a first rate of change of the first data at the first predetermined time, and to perform a first lag compensation of the first data based on the first rate of change to generate a first lag compensated first data.

Moreover, the memory in yet another embodiment may be further configured for storing instructions which, when executed by the one or more processing units, causes the one or more processing units to determine a first calibration parameter associated with the first data based on the reference data point and the first lag compensated first data and to generate a calibrated first data based on the first calibration parameter and the first lag compensated first data.

Additionally, the memory may still be further configured for storing instructions which, when executed by the one or more processing units, causes the one or more processing units to determine a second rate of change of the first data at the first predetermined time based on the second data, and to perform a second lag compensation of the first data based on the second rate of change of the first data to generate a second lag compensated first data.

In yet still another aspect, the memory may be further configured for storing instructions which, when executed by the one or more processing units, causes the one or more processing units to determine a second calibration parameter associated with the first data based on the reference data point and the second lag compensated first data, and to generate a calibrated second data based on the second calibration parameter and the second lag compensated first data.

A method in accordance with still another embodiment of the present disclosure includes, dynamically, and in particular embodiments, in real-time, obtaining reference data at a first predetermined time, receiving measured data prior to and including (or near) the first predetermined time, calculating a first calibration parameter (or parameters) using the data, calibrating the measured data based on the calibration parameter, receiving measured data at a second predetermined time, updating the calibration parameter based on all of the previous data and the newly received measured data, calibrating the newly received measured data based on the updated calibration parameter, and repeating a number of times the process of receiving new measurement data, updating the calibration parameter, calibrating the newly received measurement data, and calibrating any newly received measurement data with the fully updated calibration parameter.

A method in a further embodiment includes performing lag compensation on the measured data that is used to update the calibration parameter. Lag compensation may optionally be performed on the measured data that is calibrated. A method in a further embodiment includes filtering the measured data that is used to update the calibration parameter.

An apparatus in accordance with yet still another embodiment includes one or more processing units, and a memory for storing instructions which, when executed by the one or more processors, causes the one or more processing units to dynamically, and in particular embodiments, in real-time, obtain reference data at a first predetermined time, retrieve measured data prior to and including (or near) the first predetermined time, calculate a first calibration parameter (or parameters) using the data, calibrate the measured data based on the calibration parameter, retrieve measured data at a second predetermined time, update the calibration parameter based on all of the previous data and the newly received measured data, calibrate the newly received measured data based on the updated calibration parameter, and repeat a number of times the process of receiving new measurement data, updating the calibration parameter, calibrating the newly received measurement data, and calibrating any newly received measurement data with the fully updated calibration parameter.

A method, in one embodiment, may comprise, determining a predetermined time period characterized with a rate of change of an analyte level below a preset threshold, defining a data set associated with a monitored analyte level within the predetermined time period, determining a sensitivity value based on the defined data set, applying the determined sensitivity value to signals associated with the monitored analyte level including the defined data set, and estimating a time constant associated with an analyte sensor used to monitor the analyte level.

The preset threshold associated with the rate of change of the analyte level may be characterized by a quiescent state of the signals received from the analyte sensor.

In one aspect, the method may include receiving a reference data, and applying the sensitivity value to the signals associated with the monitored analyte level based on the received reference data.

The reference data may include a reference blood glucose measurement.

The reference data may be substantially time corresponding to one or more data in the defined data set.

The method may include calibrating the signals associated with the monitored analyte level based at least in part on the estimated time constant.

In another aspect, the method may include performing lag correction of the signals associated with the monitored analyte level based on the estimated time constant.

Further, the method may include calibrating the lag corrected signals to estimate the corresponding monitored glucose level.

In another embodiment, a computer implemented method may comprise, calibrating analyte data associated with a monitored analyte level received from an analyte sensor based on a reference measurement, determining a lag time constant associated with the calibrated analyte data, and performing lag correction of the calibrated analyte data based on the determined time lag constant.

In one aspect, the computer implemented method may include outputting the lag corrected calibrated analyte data.

The reference measurement may include a blood glucose measurement.

The reference measurement may be obtained within a predetermined time period relative to the monitored analyte level.

The predetermined time period may be less than approximately 30 minutes or greater than approximately 30 minutes.

Calibrating the analyte data may include determining a sensitivity value associated with the analyte sensor.

The sensitivity value may include a ratio of the analyte data and the corresponding reference measurement.

The analyte level may be a glucose level.

Determining the rate of change may include determining a rate of increase or a rate of decrease of the monitored analyte level for a predefined time period.

In one aspect, the computer implemented method may further include determining a rate of change of the analyte level monitored by the analyte sensor.

The rate of change of the analyte level may be determined below a predetermined threshold.

The analyte sensor may be configured to measure the analyte level based on coulometry.

The analyte sensor may be configured to measure the analyte level based on amperometry.

In yet another embodiment, an apparatus may comprise, a data communication interface, one or more processors operatively coupled to the data communication interface, and a memory for storing instructions which, when executed by the one or more processors, causes the one or more processors to determine a predetermined time period characterized with a rate of change of an analyte level below a preset threshold, define a data set associated with a monitored analyte level within the predetermined time period, determine a sensitivity value based on the defined data set, apply the determined sensitivity value to signals associated with the monitored analyte level including the defined data set, and estimate a time constant associated with an analyte sensor used to monitor the analyte level.

Various other modifications and alterations in the structure and method of operation of this invention will be apparent to those skilled in the art without departing from the scope and spirit of the invention. Although the invention has been described in connection with specific preferred embodiments, it should be understood that the invention as claimed should not be unduly limited to such specific embodiments. It is intended that the following claims define the scope of the present disclosure and that structures and methods within the scope of these claims and their equivalents be covered thereby.

What is claimed is:

1. A method, comprising:
    determining a predetermined time period characterized with a rate of change of an analyte level below a preset threshold;
    defining a data set associated with a monitored analyte level within the predetermined time period;
    determining a sensitivity value based on the defined data set;

applying, using one or more processors, the determined sensitivity value to signals associated with the monitored analyte level including the defined data set;
estimating, using the one or more processors, a time constant, associated with an analyte sensor used to monitor the analyte level, using reference data, the monitored analyte level, and the rate of change of the monitored analyte level;
performing, using the one or more processors, lag correction of the signals associated with the monitored analyte level based on the estimated time constant; and
calibrating, using the one or more processors, the lag corrected signals to estimate a corresponding monitored glucose level.

2. The method of claim 1 wherein the preset threshold associated with the rate of change of the analyte level is characterized by a state of the signals associated with the monitored analyte level.

3. The method of claim 1 including receiving a reference data, and wherein the determination of the sensitivity value is based at least in part on the received reference data.

4. The method of claim 3 wherein the reference data includes a reference blood glucose measurement.

5. The method of claim 3 wherein the reference data is substantially time corresponding to one or more data in the defined data set.

6. The method of claim 1 including calibrating the signals associated with the monitored analyte level based at least in part on the estimated time constant.

7. An apparatus, comprising:
a data communication interface;
one or more processors operatively coupled to the data communication interface; and
a memory storing instructions which, when executed by the one or more processors, causes the one or more processors to determine a predetermined time period characterized with a rate of change of an analyte level below a preset threshold, define a data set associated with a monitored analyte level within the predetermined time period, determine a sensitivity value based on the defined data set, apply the determined sensitivity value to signals associated with the monitored analyte level including the defined data set, estimate a time constant, associated with an analyte sensor used to monitor the analyte level, using reference data, the monitored analyte level, and the rate of change of the monitored analyte level, perform lag correction of the signals associated with the monitored analyte level based on the estimated time constant, and calibrate the lag corrected signals to estimate a corresponding monitored glucose level.

8. The apparatus of claim 7 wherein the preset threshold associated with the rate of change of the analyte level is characterized by a state of the signals associated with the monitored analyte level.

9. The apparatus of claim 7 including instructions which, when executed by the one or more processors, causes the one or more processors to receive a reference data, and wherein the determination of the sensitivity value is based at least in part on the received reference data.

10. The apparatus of claim 9 wherein the reference data includes a reference blood glucose measurement.

11. The apparatus of claim 9 wherein the reference data is substantially time corresponding to one or more data in the defined data set.

12. The apparatus of claim 7 including instructions which, when executed by the one or more processors, causes the one or more processors to calibrate the signals associated with the monitored analyte level based at least in part on the estimated time constant.

13. A computer implemented method, comprising:
calibrating, using one or more processors, analyte data associated with a monitored analyte level received from an analyte sensor based on a reference measurement;
determining, using the one or more processors, a rate of change of the monitored analyte level;
determining, using the one or more processors, a lag time constant, associated with the calibrated analyte data, using the reference measurement, the monitored analyte level, and the rate of change of the monitored analyte level; and
performing, using the one or more processors, lag correction of the calibrated analyte data based on the determined time lag constant.

14. The method of claim 13 including outputting the lag corrected calibrated analyte data.

15. The method of claim 13 wherein the reference measurement includes a blood glucose measurement.

16. The method of claim 13 wherein the reference measurement is obtained within a predetermined time period relative to the monitored analyte level.

17. The method of claim 16 wherein the predetermined time period is less than approximately 30 minutes or greater than approximately 30 minutes.

18. The method of claim 13 wherein calibrating the analyte data includes determining a sensitivity value associated with the analyte sensor.

19. The method of claim 18 wherein the sensitivity value includes a ratio of the analyte data and the corresponding reference measurement.

20. The method of claim 13 wherein the analyte level is glucose level.

21. The method of claim 13 wherein determining the rate of change includes determining a rate of increase or a rate of decrease of the monitored analyte level for a predefined time period.

22. The method of claim 13 wherein the rate of change of the analyte level is determined below a predetermined threshold.

* * * * *